(12) United States Patent
Ainsworth et al.

(10) Patent No.: US 6,913,607 B2
(45) Date of Patent: Jul. 5, 2005

(54) SELF-CLOSING SURGICAL CLIP FOR TISSUE

(75) Inventors: Stephen Ainsworth, Los Gatos, CA (US); Jianhua Yang, Mountain View, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/847,947

(22) Filed: May 2, 2001

(65) Prior Publication Data

US 2002/0165561 A1 Nov. 7, 2002

Related U.S. Application Data

(63) Continuation-in-part of application No. 09/847,716, filed on May 1, 2001, now abandoned.

(51) Int. Cl.$^7$ .............................................. A61B 17/08
(52) U.S. Cl. ...................... 606/151; 606/153; 606/155; 606/213; 606/221
(58) Field of Search ................................. 606/151, 155, 606/213, 221, 153

(56) References Cited

U.S. PATENT DOCUMENTS

| | | | | |
|---|---|---|---|---|
| 3,570,497 A | * | 3/1971 | Lemole ....................... | 606/151 |
| 3,874,388 A | * | 4/1975 | King et al. .................. | 606/232 |
| 3,958,576 A | * | 5/1976 | Komiya ....................... | 606/140 |
| 4,485,816 A | | 12/1984 | Krumme | |
| 4,586,503 A | | 5/1986 | Kirsch et al. | |
| 4,929,240 A | | 5/1990 | Kirsch et al. | |
| 4,983,176 A | * | 1/1991 | Cushman et al. ............ | 606/142 |
| 4,994,069 A | | 2/1991 | Ritchart et al. ............. | 606/191 |
| 5,002,563 A | | 3/1991 | Pyka et al. | |
| 5,007,920 A | | 4/1991 | Torre | |
| 5,158,566 A | | 10/1992 | Pianetti | |

(Continued)

FOREIGN PATENT DOCUMENTS

| | | |
|---|---|---|
| WO | WO 99/62406 A2 | 12/1999 |
| WO | WO 99/62409 A1 | 12/1999 |
| WO | WO 01/74254 A1 | 10/2001 |

OTHER PUBLICATIONS

"VCS Clip Applier System," published in 1995 by Auto Suture Company, a Division of U.S. Surgical Corporation (8 pages).
Emery et al. "Suture Techniques for MIDCAB Surgery" Chapt. 12, pp. 87–91.
Wylie, Edwin J. et al., Manual of Vascular Surgery, (Springer–Verlag New York), (1980) Table of contents only.
International Search Report PCT/US02/14261 (Jun. 17, 2003).
Written Opinion PCT/US02/14261 (Oct. 28, 2003).
International Preliminary Examination Report PCT/US02/14261 (Apr. 7, 2004).

*Primary Examiner*—Rodney M. Lindsey
(74) *Attorney, Agent, or Firm*—Tom Berry; Jeffrey J. Hohenshell

(57) ABSTRACT

A self-closing fastener is described that comprises a clip passable through a tissue opening. The fastener is adapted for holding by a mechanism in an open configuration for passing through the tissue, followed by releasing the fastener from the holding mechanism, allowing the clip to remain in the tissue in a shape that can clip two or more locations on the tissue. The fastener and delivery devices are particularly useful for tissue approximation, such as anastomosis. When used for anastomosis, the inventive clips provide intima-to-intima contact with a minimal amount of intraluminal exposure.

70 Claims, 16 Drawing Sheets

U.S. PATENT DOCUMENTS

| | | | |
|---|---|---|---|
| 5,236,440 A | | 8/1993 | Hlavacek |
| 5,304,204 A | | 4/1994 | Bregen |
| 5,366,479 A | | 11/1994 | McGarry et al. |
| 5,423,821 A | * | 6/1995 | Pasque ............... 606/151 |
| 5,450,860 A | | 9/1995 | O'Connor |
| 5,474,557 A | | 12/1995 | Mai |
| 5,597,378 A | | 1/1997 | Jervis |
| 5,645,568 A | | 7/1997 | Chervitz et al. ............ 606/228 |
| 5,715,987 A | | 2/1998 | Kelley et al. |
| 5,766,189 A | | 6/1998 | Matsumo |
| 5,810,851 A | | 9/1998 | Yoon |
| 5,879,371 A | | 3/1999 | Gardiner et al. |
| 5,891,160 A | | 4/1999 | Williamson, IV et al. |
| 5,893,886 A | * | 4/1999 | Zegdi et al. ............ 606/153 |
| 5,941,888 A | | 8/1999 | Wallace et al. ........... 606/108 |
| 5,972,024 A | * | 10/1999 | Northrup et al. .......... 606/151 |
| 6,056,751 A | | 5/2000 | Fenton, Jr. |
| 6,074,401 A | | 6/2000 | Gardiner et al. |
| 6,077,291 A | | 6/2000 | Das |
| 6,113,611 A | | 9/2000 | Allen et al. |
| 6,149,658 A | | 11/2000 | Gardiner et al. |
| 6,152,937 A | * | 11/2000 | Peterson et al. ............ 606/153 |
| 6,159,225 A | * | 12/2000 | Makower ................. 606/155 |
| 6,165,183 A | | 12/2000 | Kuehn et al. |
| 6,165,185 A | | 12/2000 | Shennib et al. |
| 6,171,320 B1 | | 1/2001 | Monassevitch |
| 6,197,037 B1 | | 3/2001 | Hair |
| 6,217,611 B1 | | 4/2001 | Klostermeyer ............ 623/2.38 |
| 6,254,615 B1 | * | 7/2001 | Bolduc et al. ............. 606/142 |
| 6,425,900 B1 | * | 7/2002 | Knodel et al. ............. 606/151 |
| 6,451,048 B1 | * | 9/2002 | Berg et al. ................ 623/1.13 |
| 6,514,265 B2 | | 2/2003 | Ho et al. |
| 6,551,332 B1 | | 4/2003 | Nguyen et al. |
| 6,607,541 B1 | | 8/2003 | Gardiner et al. |
| 6,613,059 B2 | | 9/2003 | Schaller et al. |
| 6,641,593 B1 | | 11/2003 | Schaller et al. |
| 6,660,015 B1 | * | 12/2003 | Berg et al. ................ 606/153 |
| 6,695,859 B1 | | 2/2004 | Golden et al. |
| 6,702,826 B2 | | 3/2004 | Liddicoat et al. .......... 606/151 |
| 6,776,785 | * | 8/2004 | Yencho et al. ............. 606/153 |
| 2001/0018592 | | 8/2001 | Schaller et al. |
| 2001/0018593 | * | 8/2001 | Nguyen et al. ............ 606/151 |
| 2002/0099395 | * | 7/2002 | Acampora et al. .......... 606/151 |
| 2003/0074012 | | 4/2003 | Nguyen et al. |
| 2004/0111099 | | 6/2004 | Nguyen et al. |

* cited by examiner

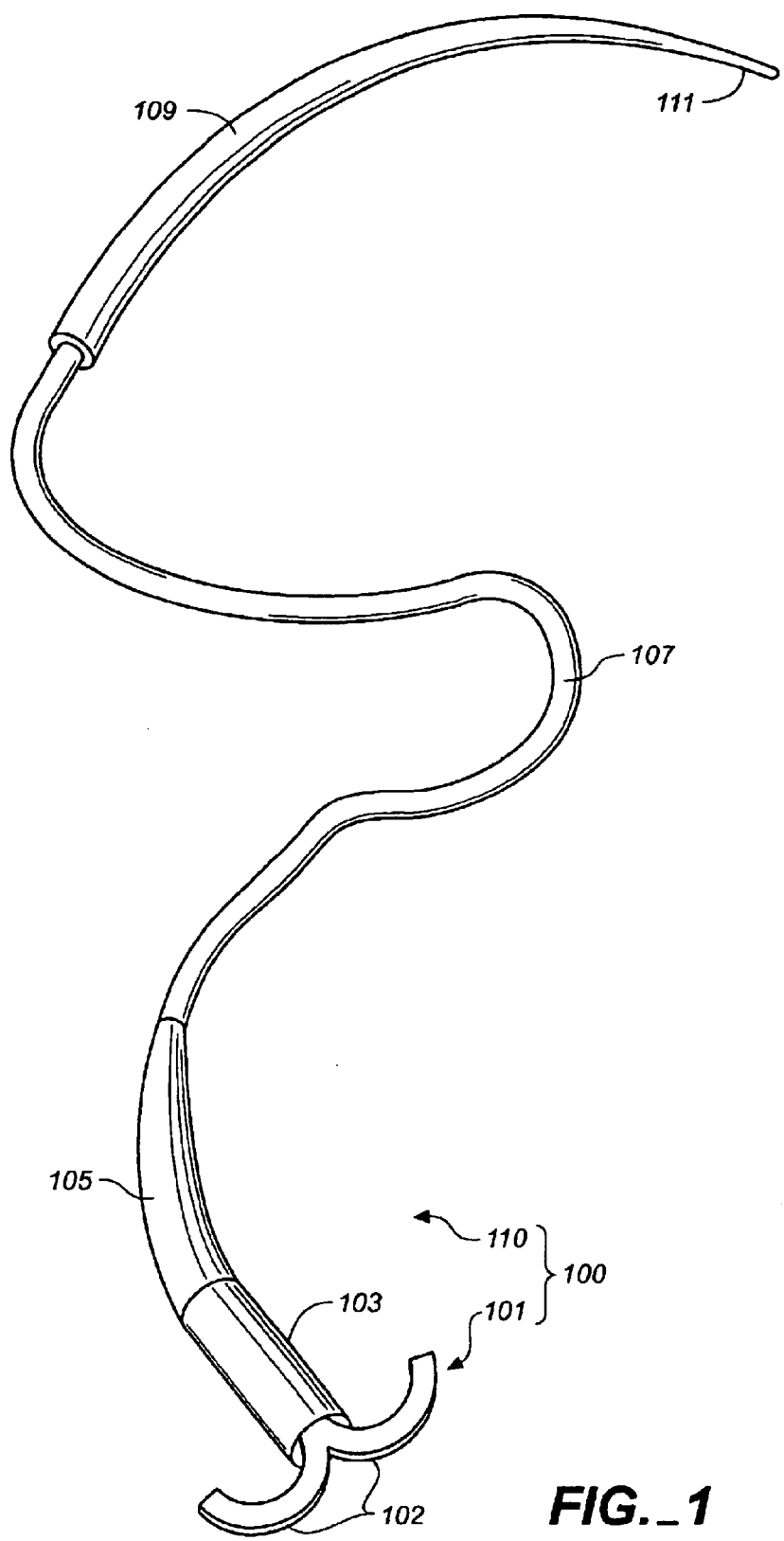
FIG._1

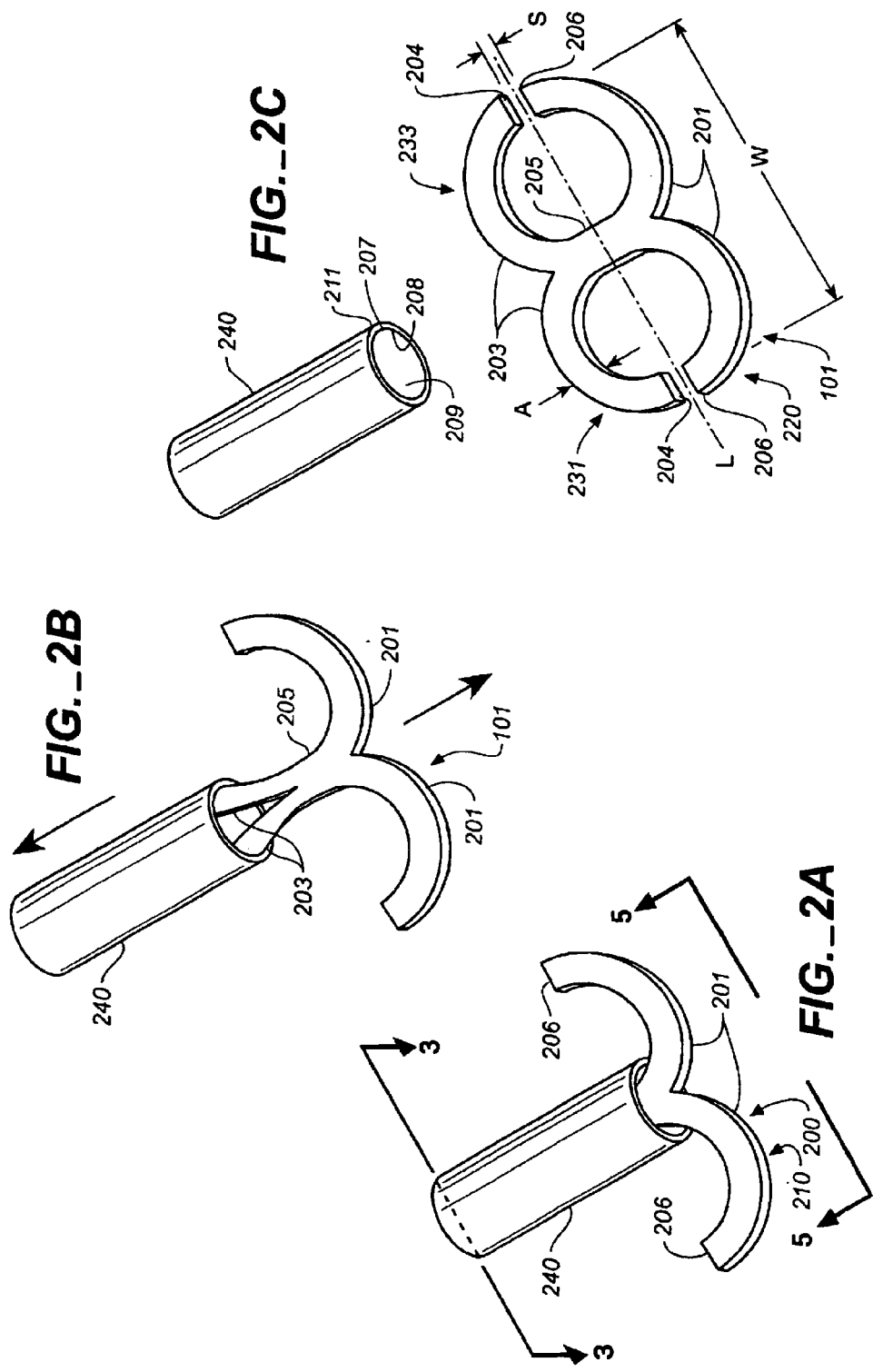

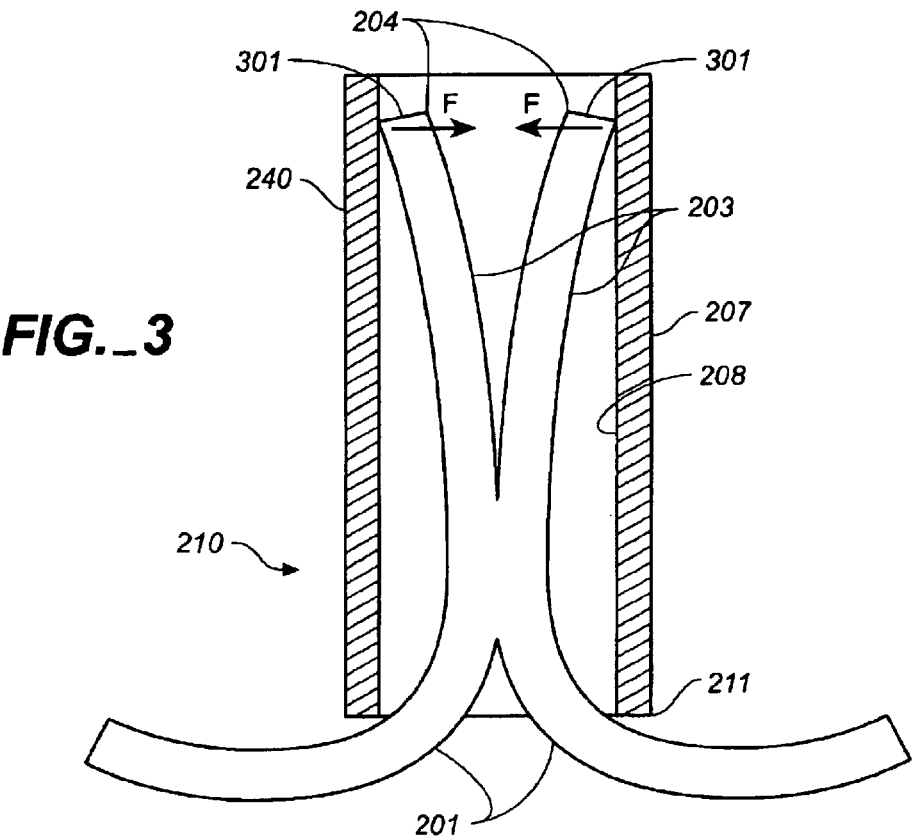
FIG._3
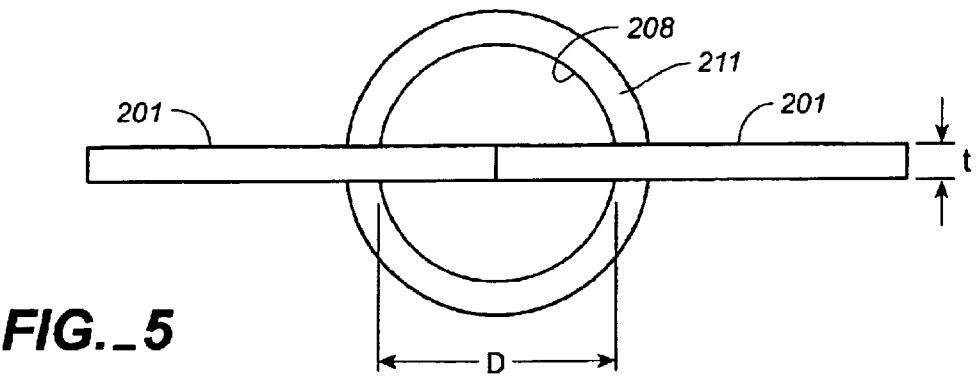
FIG._5

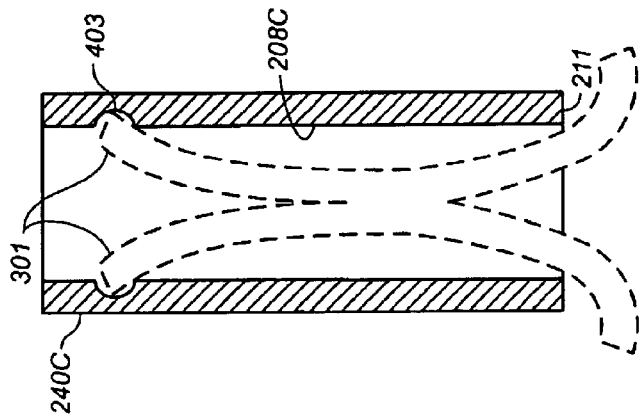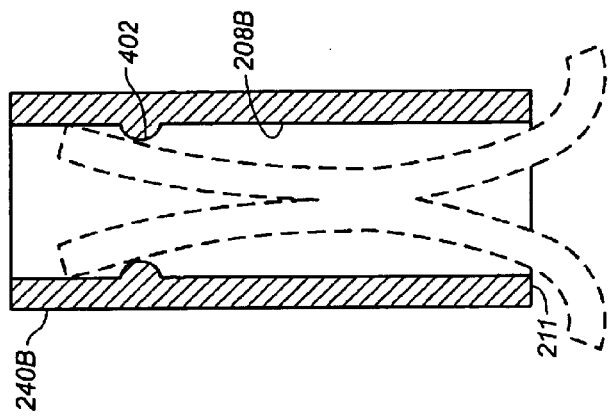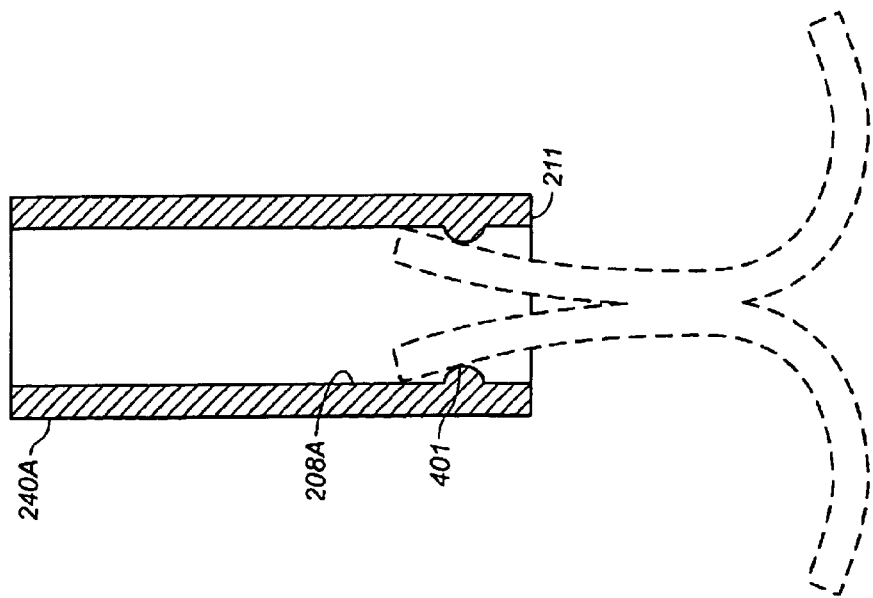

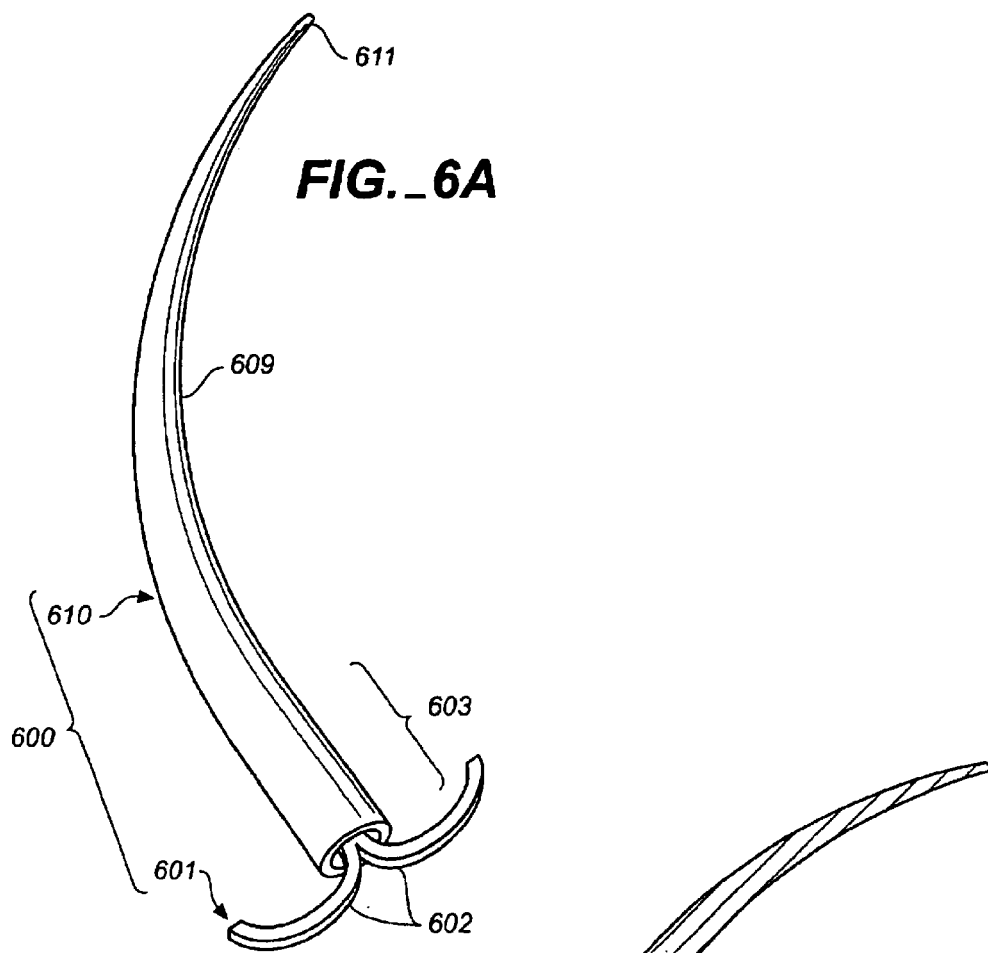
FIG._6A
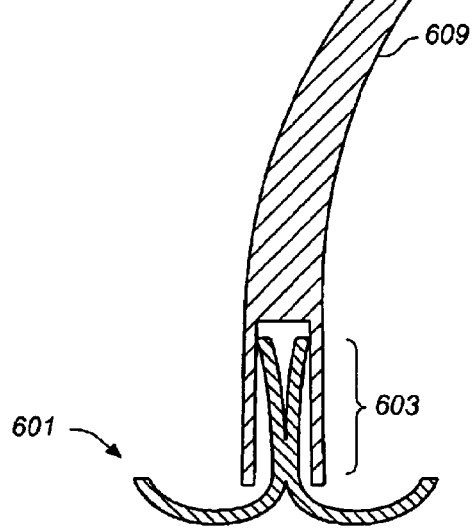
FIG._6B

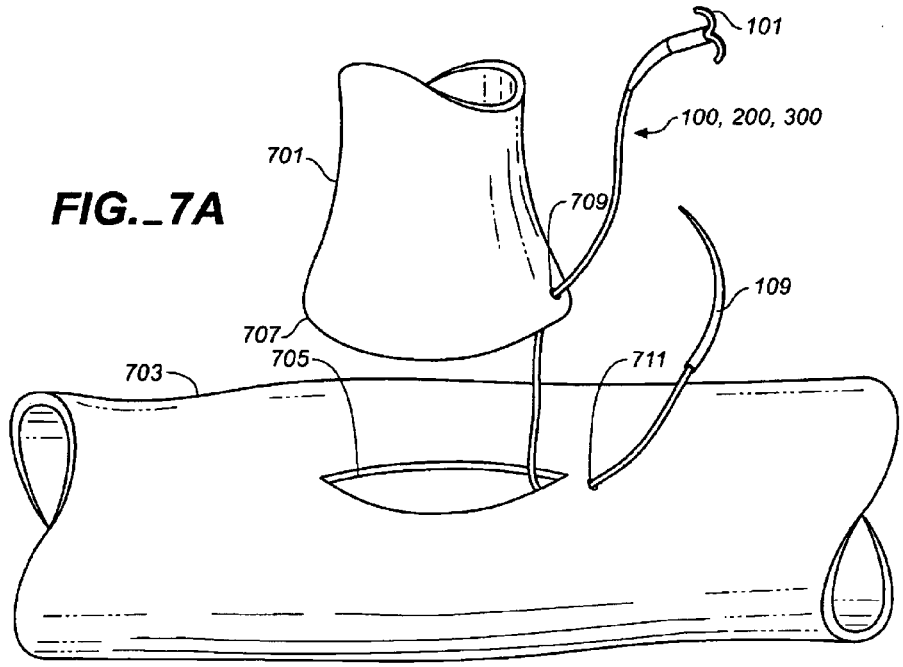
FIG._7A
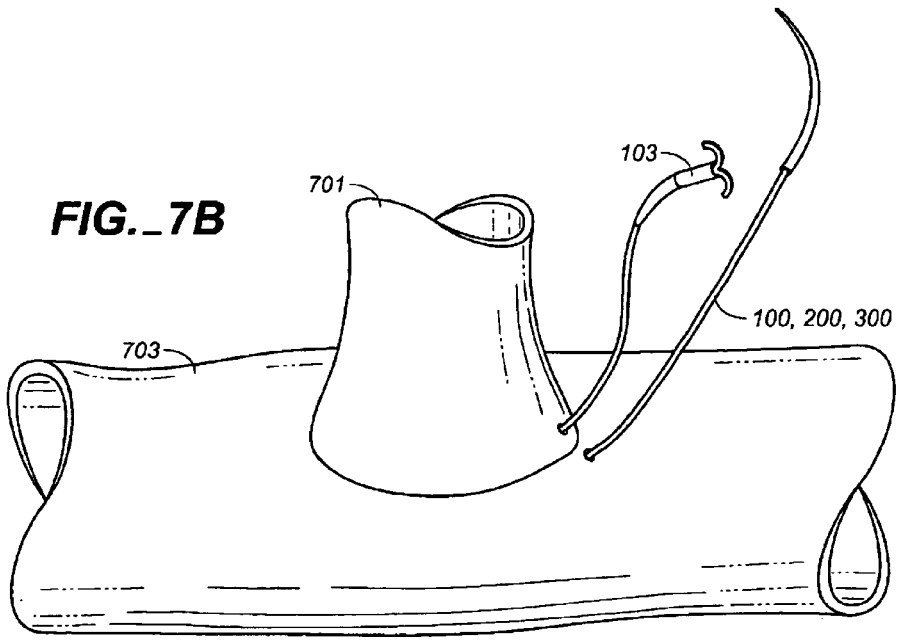
FIG._7B

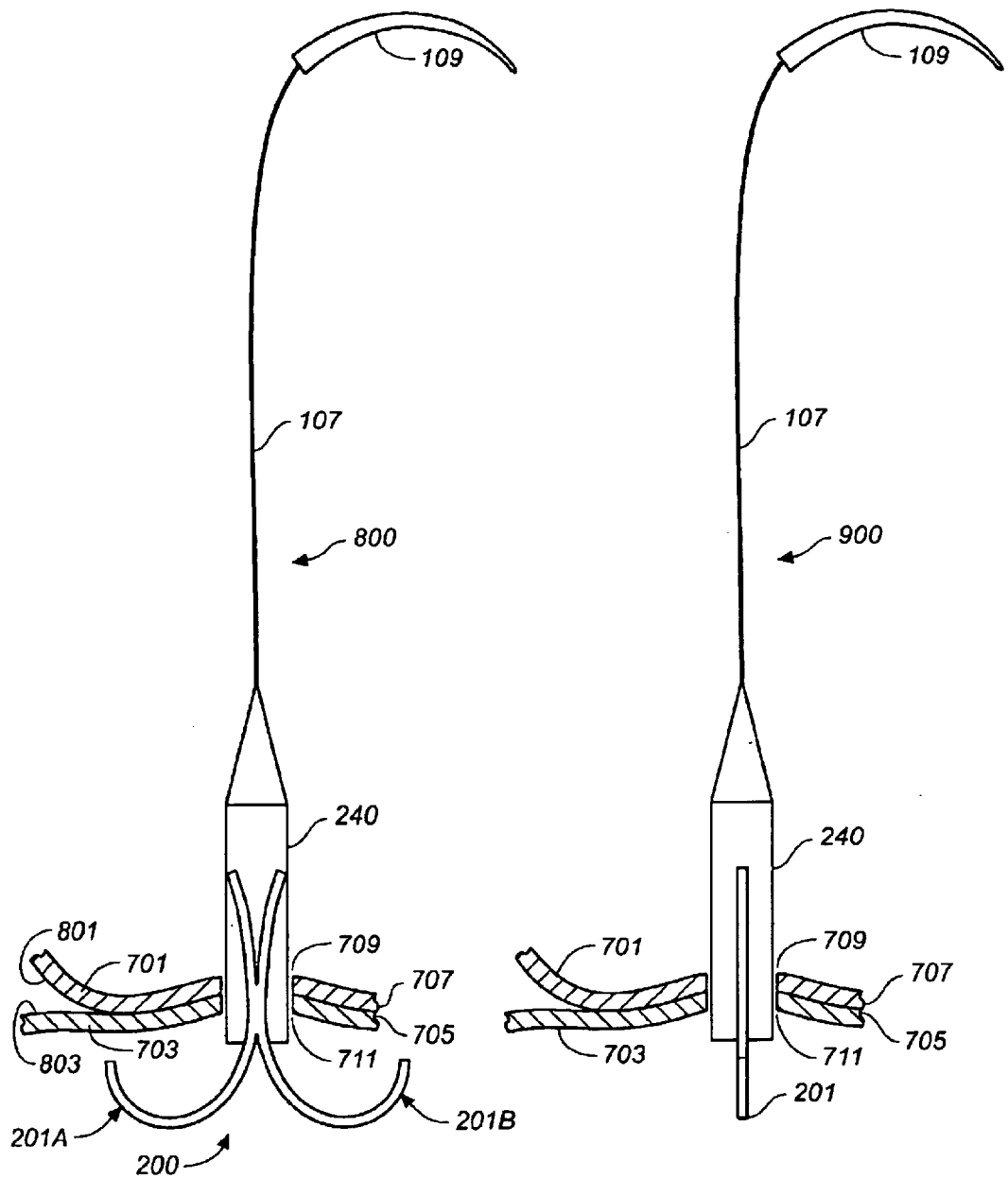

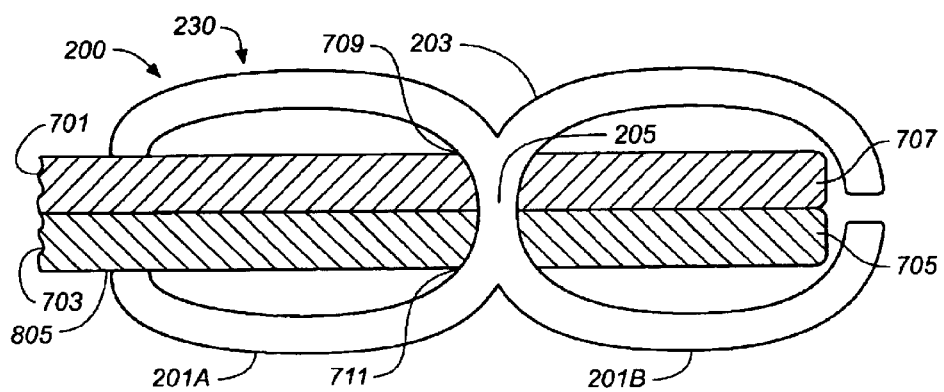
FIG._8B
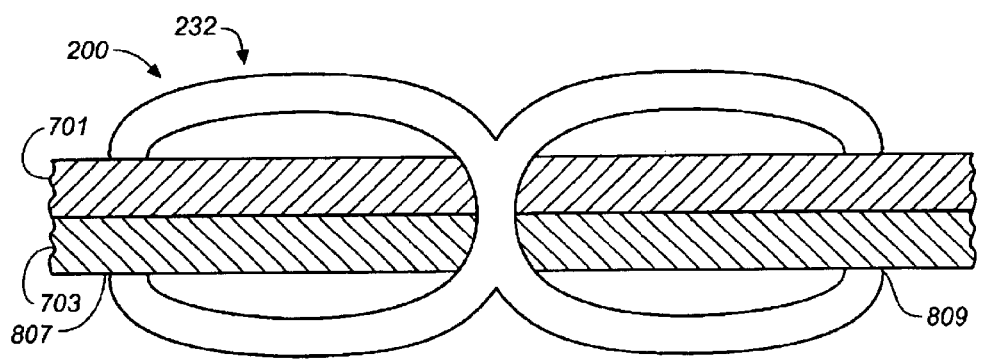
FIG._9B

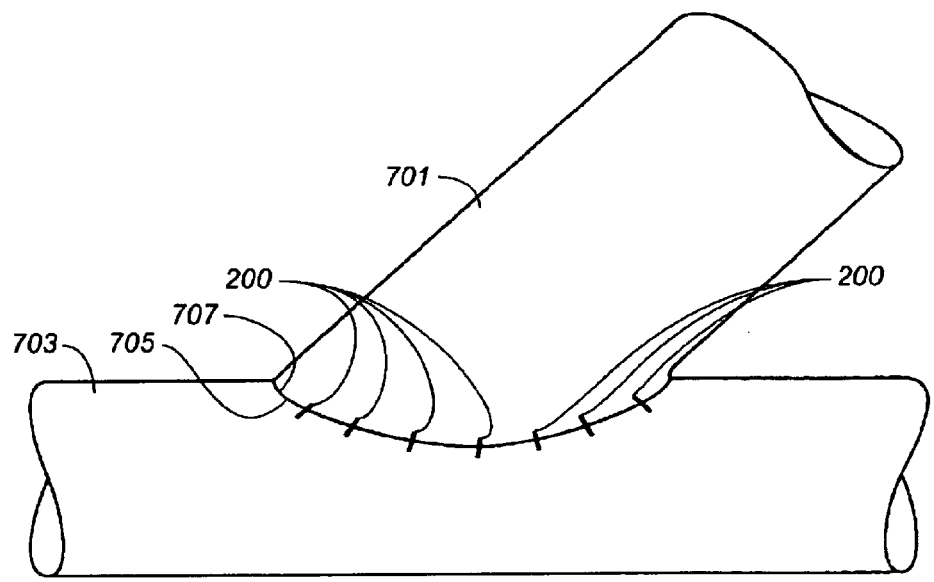
FIG._8C
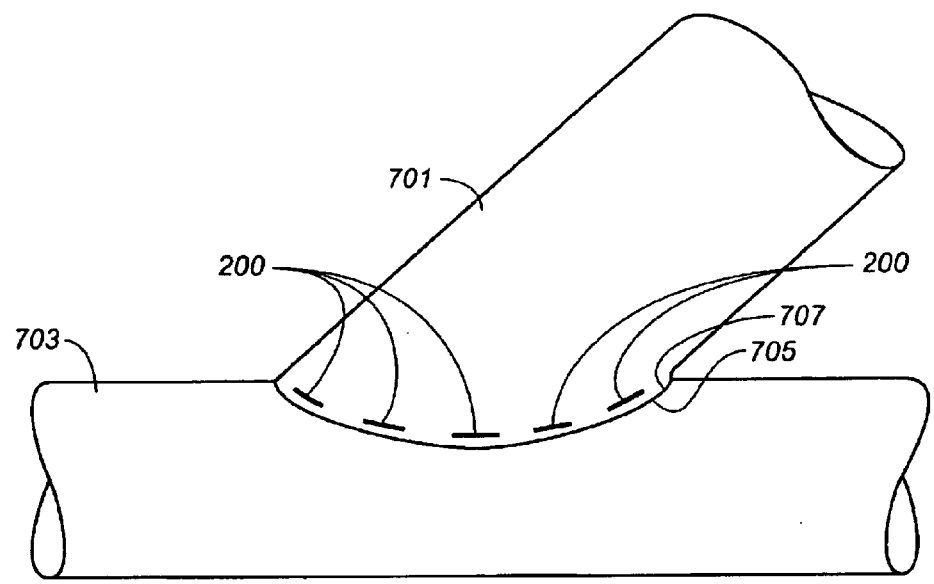
FIG._9C

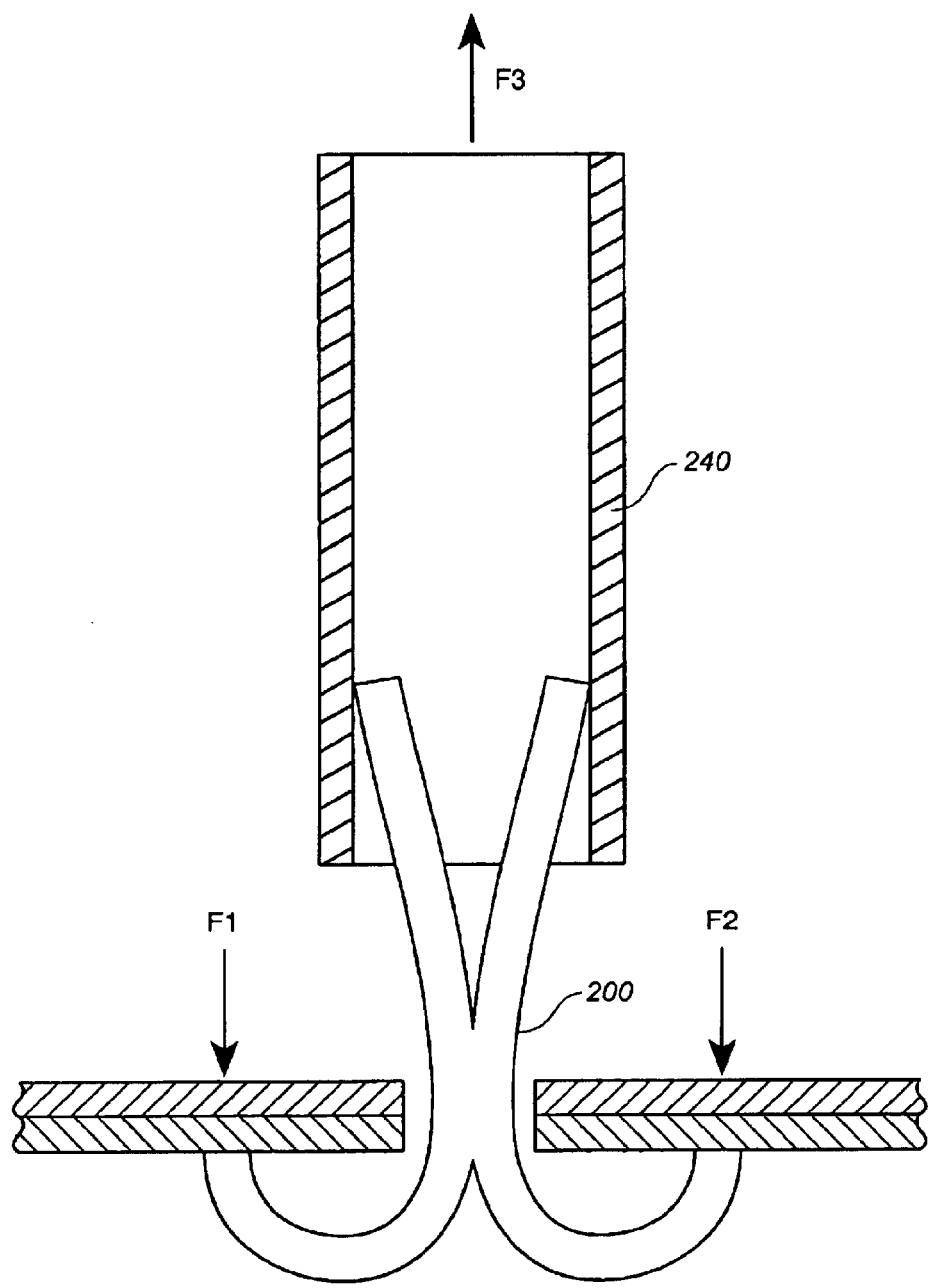
FIG._10

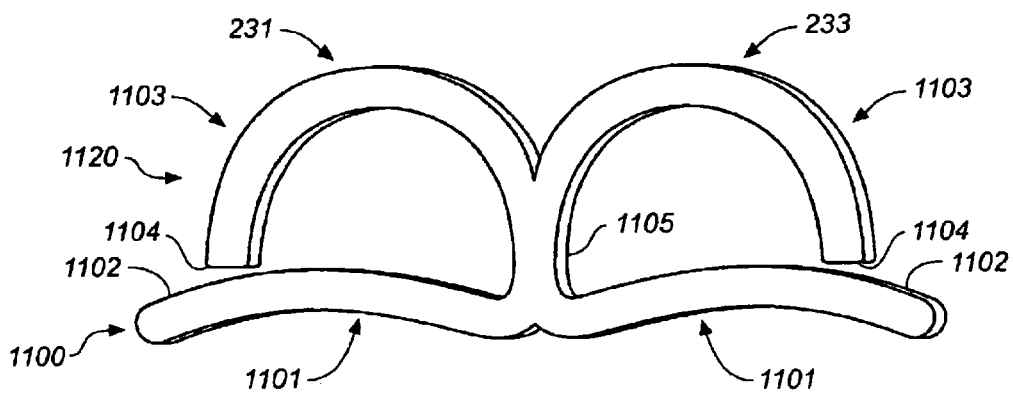
FIG._11A
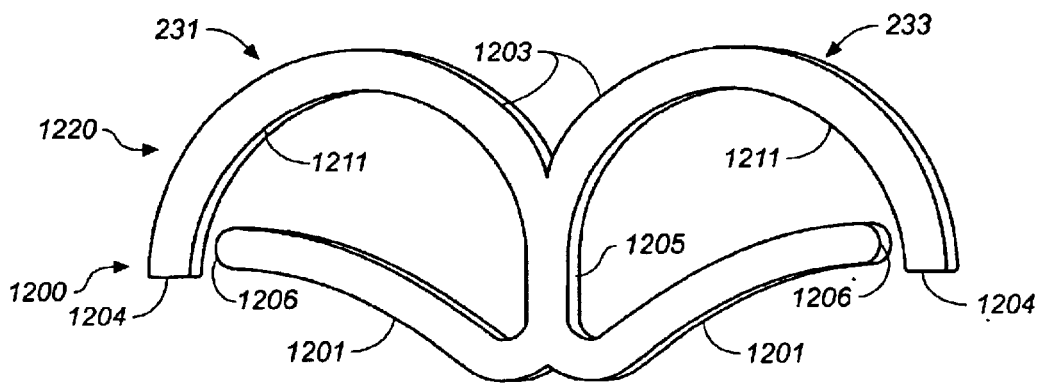
FIG._12A
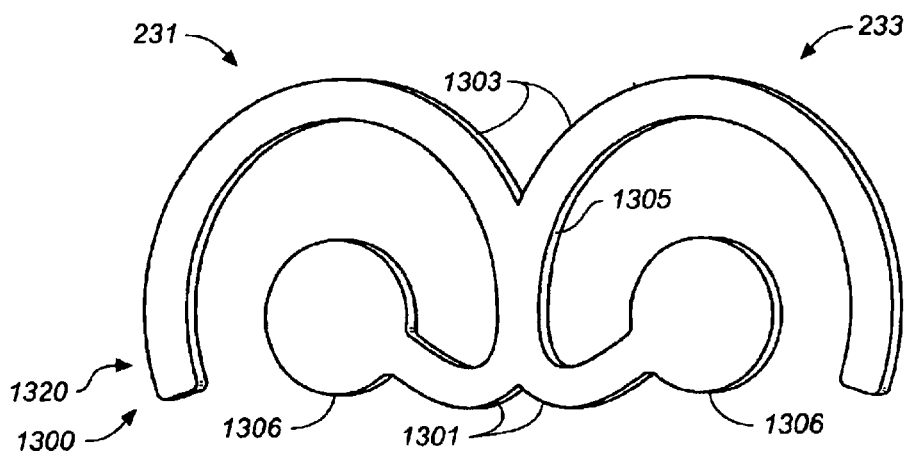
FIG._13A

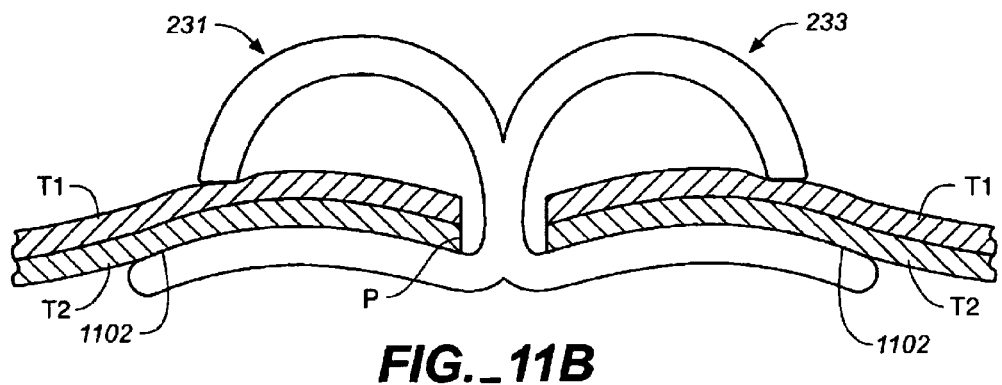
FIG._11B
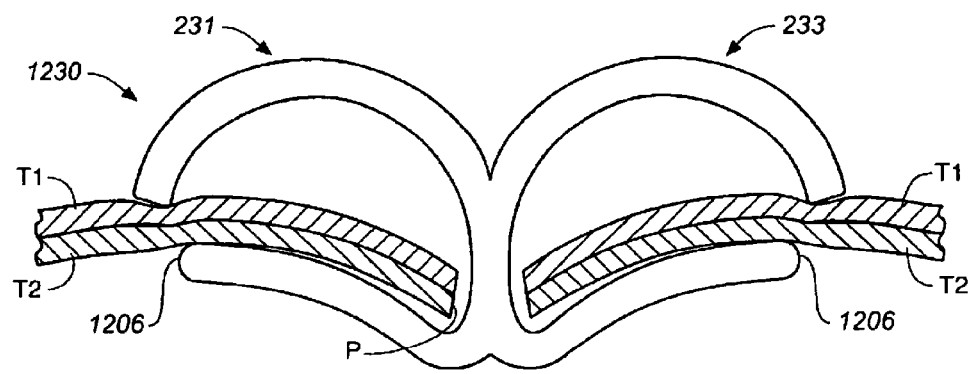
FIG._12B
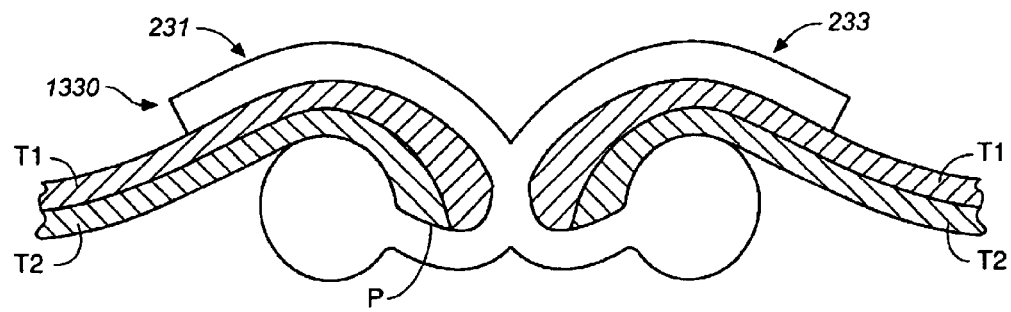
FIG._13B

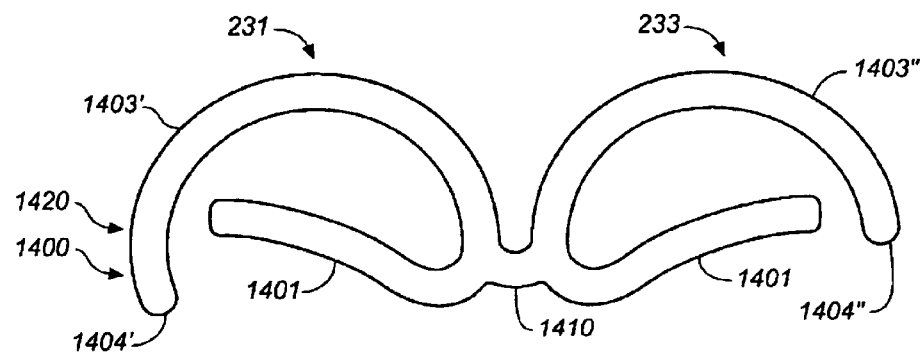
FIG._14
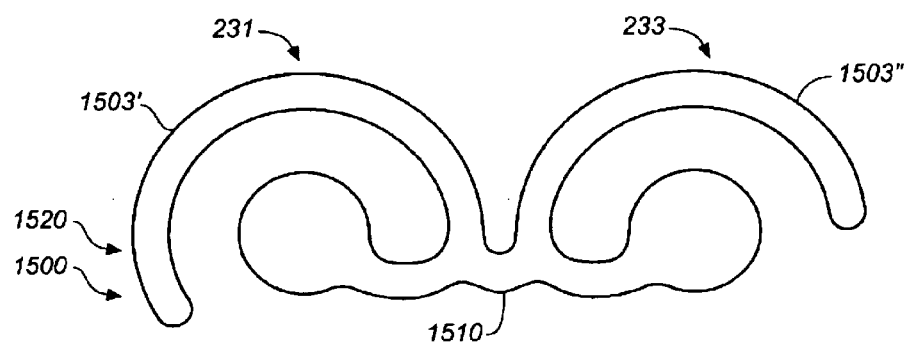
FIG._15
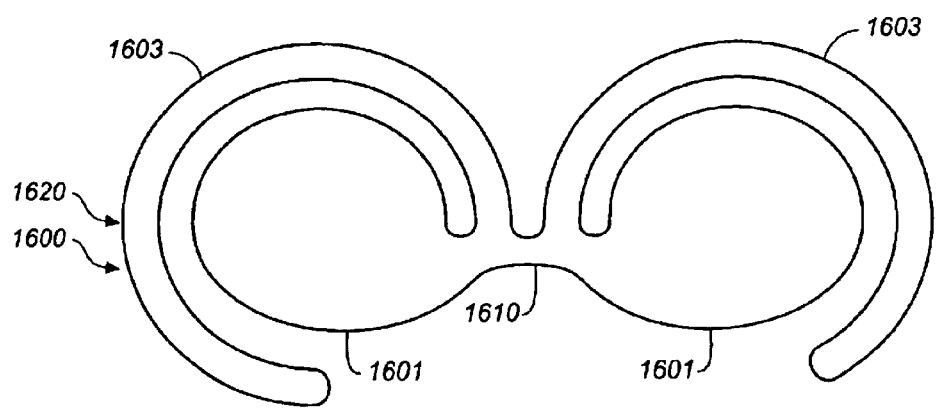
FIG._16

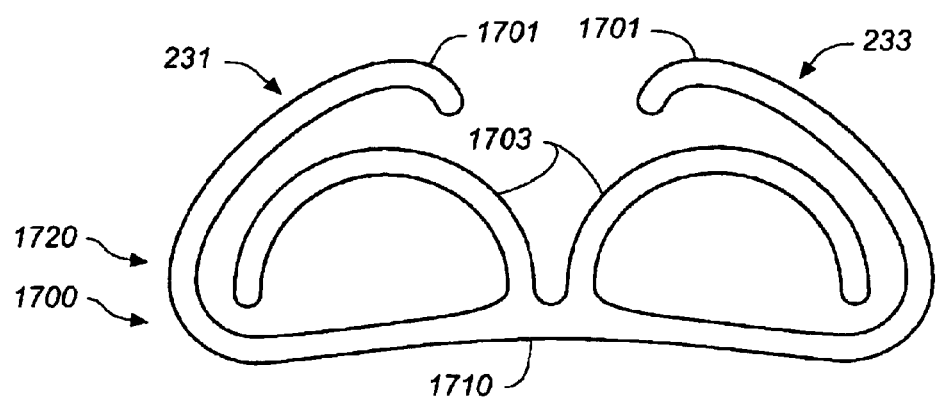
FIG._17A
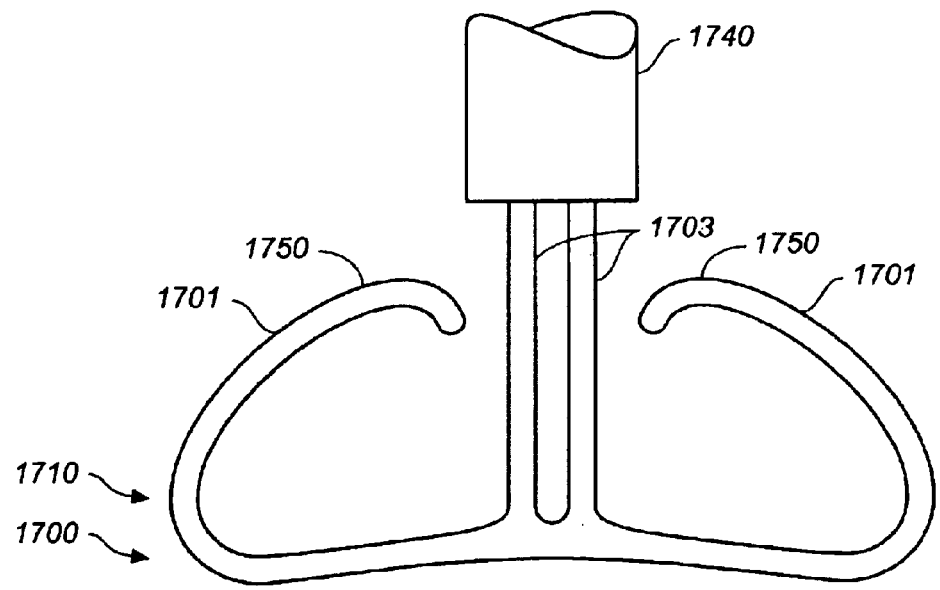
FIG._17B

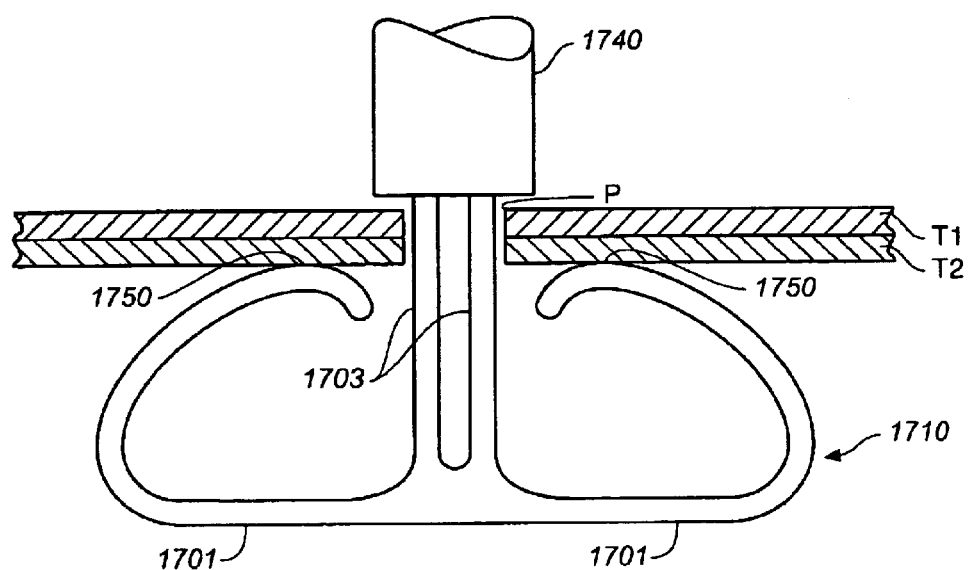
FIG._17C
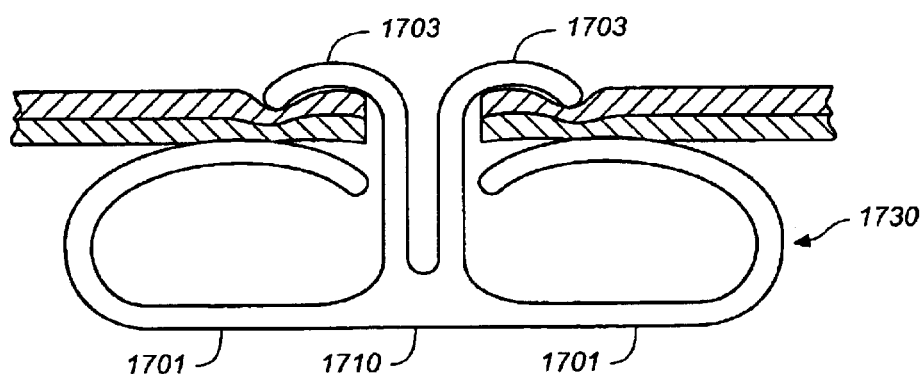
FIG._17D

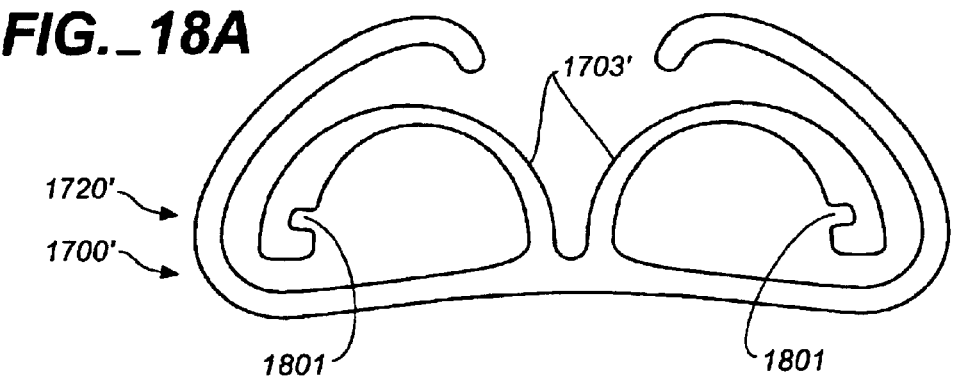
FIG._18A
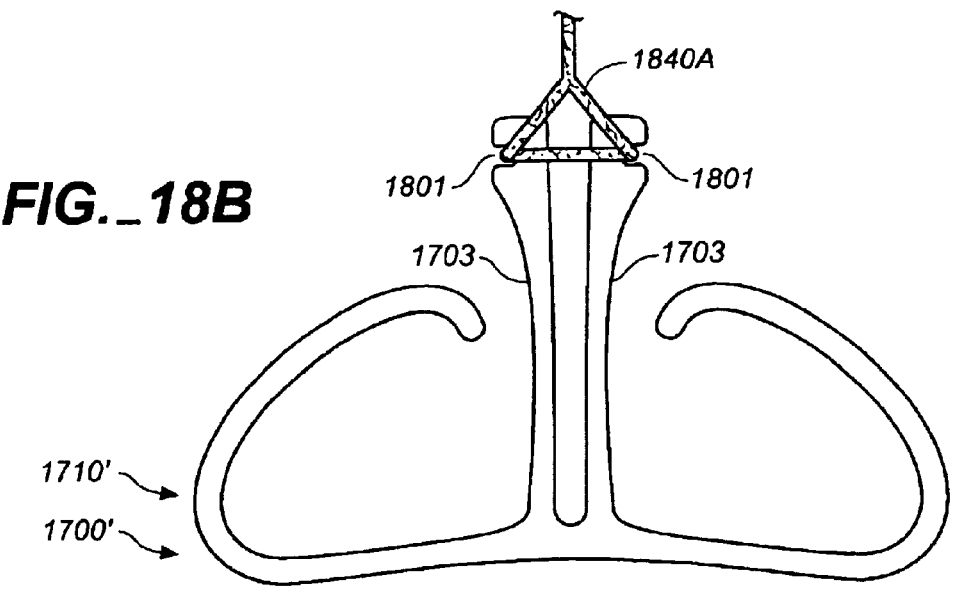
FIG._18B
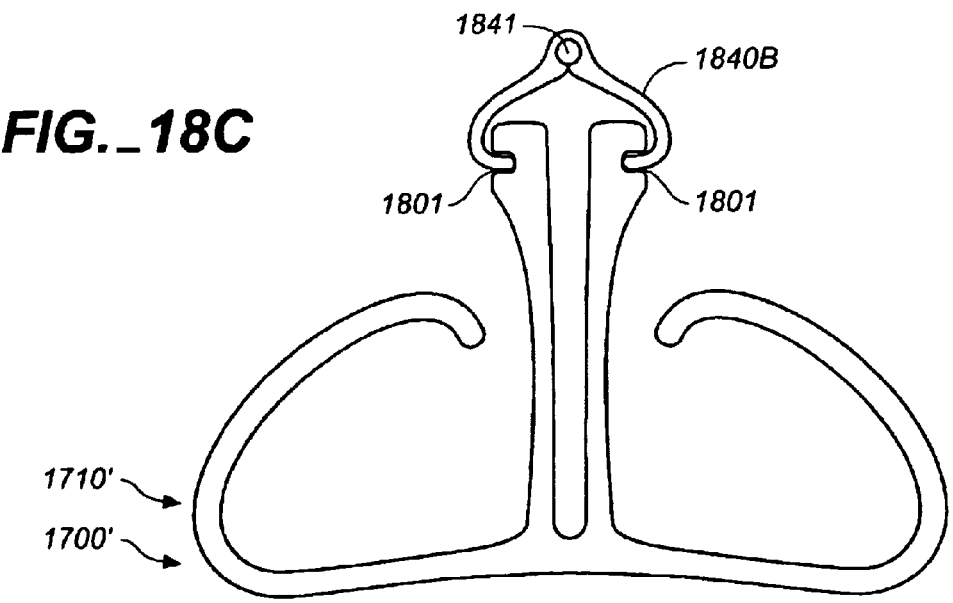
FIG._18C

SELF-CLOSING SURGICAL CLIP FOR TISSUE

CROSS REFERENCE TO RELATED APPLICATION(S)

This application is a continuation-in-part of U.S. patent application Ser. No. 09/847,716 entitled "Self-Closing Surgical Clip for Tissue" and filed on May 1, 2001 now abandoned.

FIELD OF THE INVENTION

The present invention relates to devices and methods for sealing tissue punctures. More specifically, the present invention is directed to devices and methods for approximating wound edges of vessel openings to affect hemostasis.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, typically 5–10 millimeters, and sometimes up to as much as 20 millimeters. A number of such cannulas are inserted for any given operation.

A viewing instrument, typically including a miniature video camera or optical telescope, is inserted through one of these cannulas and a variety of surgical instruments and refractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine, or abdominal wall hernia.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from DACRON® (polyester fibers) or TEFLON® (fluorocarbon fibers)) or are prepared as autografts (from the patient's own tissues) or heterografts (from the tissues of animals) or a combination of tissues, semi-synthetic tissues and or alloplastic materials. A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swaged on" to a long, trailing suture material. The needle must be precisely controlled and accurately placed through both the graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

A parachuting technique may be used to align the graft with the artery in an end-to-side anastomosis procedure. One or multiple sutures are attached to the graft and artery and are used to pull or "parachute" the graft vessel into alignment with an opening formed in a sidewall of the artery. A drawback to this procedure is the difficulty in preventing the suture from tangling and the time and surgical skill required to tie individual knots when using multiple sutures. Due to space requirements, this procedure is generally limited to open surgery techniques.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by applying an instrument about the tissue in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be properly positioned with respect to each other, for example by skewering the tissues with a needle as discussed above in common suturing techniques or with forceps to bring the tissues together. It is extremely difficult to perform such positioning techniques in minimally invasive procedures.

Therefore, there is currently a need for other tissue connecting systems.

SUMMARY OF THE INVENTION

The present invention involves apparatus and methods for connecting material, at least one of which is tissue. The invention may, for example, be used to secure one vessel to another, such as in a vascular anastomosis.

According to one aspect of the invention a fastener is provided to a tissue having an opening for clipping the tissue. In one embodiment, the fastener includes two clips connected to one another, where each of the two clips has a proximal arm and a distal arm for compressing the tissue on a proximal and distal surface. The proximal arm is springably movable between a restrained configuration and a released configuration. The proximal arms are placed in the restrained configuration in a direction generally perpendicular to the distal arms, and return to the released configuration towards the proximal arms, providing a compressive force on the tissue.

According to another aspect of the present invention, a fastener is held in an open configuration by a delivery mechanism that holds and retains the fastener in an open configuration. The fastener has opposable members that can be opened for insertion through a tissue piercing and can be closed to provide a compressive force at several location simultaneously. Another aspect is to provide a greater closing force and/or a closing force over a greater area with a self-closing clip.

According to yet another aspect of the invention, a fastener is provided that can be delivered to a wound site and can be used to clip tissues to promote intima-to-intima contact. Another aspect is the providing of a fastener that reduces intraluminal metallic component contact.

Yet another aspect of the present invention is to provide clips that can be used to perform anastomosis with fewer clips that other fastener systems.

According to another aspect of the invention, a tissue approximation device is provided that facilitates interrupted anastomosis without know tying and which promotes the dilation and growth of the vessel. Another aspect of the invention supplies a self-closing fastener to tissue that securely anchors the fastener to the tissue with a controlled approximation force.

It is yet another aspect of the present invention to provide a method for fastening tissue with a clip delivered to said tissue. In one embodiment the clip is releasably retained in a holder that is connected to a piercing member. The method includes passing the holder through said piercing, seating a stopper portion of the coupled clip against said first surface, and decoupling said clip, such that said at least one terminator arms returns towards said disengaged configuration and opposes said stopper across said tissue.

The above is a brief description of some deficiencies in the prior art and advantages of the present invention. Other features, advantages, and embodiments of the invention will be apparent to those skilled in the art from the following description, accompanying drawings, and claims.

A further understanding of the invention can be had from the detailed discussion of specific embodiments below. For purposes of clarity, this discussion refers to devices, methods, and concepts in terms of specific examples. However, the method of the present invention may operate with a wide variety of types of devices. It is therefore intended that the invention not be limited by the discussion of specific embodiments.

For purposes of clarity, the invention is described in terms of systems that include many different innovative components and innovative combinations of components. No inference should be taken to limit the invention to combinations containing all of the innovative components listed in any illustrative embodiment in this specification.

Additional objects, advantages, aspects and features of the present invention will become apparent from the description of preferred embodiments, set forth below, which should be taken in conjunction with the accompanying drawings, a brief description of which follows.

BRIEF DESCRIPTION OF THE DRAWINGS

The invention will be better understood by reference to the Figures of the drawings wherein:

FIG. 1 is a perspective of a tissue connector assembly of the present invention;

FIGS. 2A–2C are perspective views showing the removal of a fastener from a holder, where FIG. 2A shows the fastener in an open configuration and stored in the holder, FIG. 2B shows the fastener in an open configuration and partially pulled out of the holder just prior to fastening, and FIG. 2C shows the fastener released from the holder and returned to the closed configuration;

FIG. 3 is cross-sectional view 3—3 from FIG. 2A of the fastener and holder of the present invention;

FIGS. 4A–4C are three alternative restraint mechanism embodiments along cross-section view 3—3;

FIG. 5 is a distal end view 5—5 from FIG. 2A of the fastener and holder of the present invention;

FIGS. 6A–6B are views of an alternative tissue connector assembly of the present invention having a fastener retained by a holder integral to a piercing member, where FIG. 6A is a perspective view and FIG. 6B is a cross-sectional view of the alternative assembly;

FIGS. 7A–7B show a tissue connector assembly of the present invention threaded through two tissues, where FIG. 7A is a perspective view of the assembly threaded through the end of a graft vessel and near an opening created in a second vessel for performing an anastomosis, and FIG. 7B is a perspective view of the vessels positioned for performing the anastomosis;

FIGS. 8A–8C show the placement of a fastener in a radial configuration, where FIG. 8A is a cross-sectional view of a clip and the tissue prior to fastening, FIG. 8B is a cross-sectional view after fastening, and FIG. 8C shows the placement of radially arranged fasteners about the anastomosis;

FIGS. 9A–9C show the placement of a fastener in a circumferential fastening configuration, where FIG. 9A is a cross-sectional view of a clip and the tissue prior to fastening, FIG. 9B is a cross-sectional view after fastening, and FIG. 9C shows the placement of circumferentially arranged fasteners about the anastomosis;

FIG. 10 illustrates the action required for separating the fastener from the holder;

FIGS. 11A–11B are views of a first alternative fastener embodiment, where FIG. 11A is a view of the fastener in a closed configuration, and FIG. 11B is a view of the fastener as it clips tissue in a fastened configuration;

FIGS. 12A–12B are views of the fastener of a second alternative fastener embodiment, where FIG. 12A is a view of the fastener in a closed configuration, and FIG. 12B is a view of the fastener as it clips tissue in a fastened configuration;

FIGS. 13A–13B are views of a third alternative fastener embodiment, where FIG. 13A is a view of the fastener in a closed configuration, and FIG. 13B is a view of the fastener as it clips tissue in a fastened configuration;

FIG. 14 is a view of a fourth alternative fastener embodiment in a closed configuration;

FIG. 15 is a view of a fifth alternative fastener embodiment in a closed configuration;

FIG. 16 is a view of a sixth alternative fastener embodiment in a closed configuration;

FIGS. 17A–D are views of an seventh alternative fastener embodiment in a closed configuration, where FIG. 17A is a view of the fastener in a closed configuration, FIG. 17B is a view of the fastener with terminator arms restrained in an open configuration, FIG. 17C is a view of the fastener placed for clipping, and FIG. 17D is a view of the fastener in a fastened configuration; and FIGS. 18A–C are frontal views of a eighth alternative fastener, where FIG. 18A is a view of the fastener in a closed configuration, FIG. 18B is a view of the fastener in an open configuration as restrained with suture, and FIG. 18C is a view of the fastener restrained with a restraining clip.

Reference symbols are used in the Figures to indicate certain components, aspects or features shown therein, with reference symbols common to more than one Figure indicating like components, aspects or features shown therein. The reference symbols used herein are not to be confused with any reference symbols used in the items that have been incorporated herein by reference.

DESCRIPTION OF SPECIFIC EMBODIMENTS

Referring now to the drawings, and first to FIG. 1, a tissue connector assembly constructed according to the principles of the present invention is shown and generally indicated with reference numeral 100. The tissue connector assembly 100 may be used to manipulate and align tissues, or tissue and graft with respect to each other and thereafter connect the tissues together (FIGS. 6–8). As used herein, the term graft includes any of the following: homografts, xenografts, allografts, alloplastic materials, and combinations of the foregoing. The tissue connector assembly and connectors of the present invention are generally useful for attaching tissues and, as will become apparent upon reflection of the present disclosure, can be used for a variety of medical procedures or can be modified within the scope of the present invention to perform such procedures. Thus the tissue connector assembly 100 may be used as illustrated in FIGS. 7, 8 and 9 in vascular surgery to replace or bypass a diseased, occluded, or injured artery by connecting a graft vessel 701 to a coronary artery 703 or vein in an anastomosis, for example. The tissue connector assembly 100 may be used in open surgical procedures or in minimally invasive or endoscopic procedures for attaching tissue located in the chest, abdominal cavity, or retroperitoneal space. These examples, however, are provided for illustration and are not meant to be limiting.

In the embodiment shown in FIG. 1, tissue connector assembly 100 generally comprises a fastener 101 and a fastener delivery device 110. Delivery device 110 includes a holder 103 that is adapted to retain fastener 101 and is attached to a penetrating member or needle 109. As shown in FIG. 1, holder 103 is attached to needle 109 through a transition piece 105 to a flexible member 107. In general, the needle 109 has a sharp pointed tip 111 at its distal end for penetrating tissue. The needle 109 may be bent as shown in FIG. 1, for example. The distal end of the needle 109 is preferably rigid to facilitate penetration of tissue. The remaining length of the needle 109 may be rigid or flexible to facilitate movement of the needle through the tissue as further described below. The tip 111 of the needle 109 may be conical, tapered, or grounded to attain a three or four facet tip, for example. The needle 109 may be made from stainless steel or any other suitable material, such as a polymeric material. It is to be understood that the needle 109 may have a shape or radius of curvature other than the one shown, without departing from the scope of the invention. The needle 109 may be integrally formed with holder 103 or may be swaged, welded, threadably attached, or attached by any other suitable means to the holder. In some embodiments of the invention flexible member 107 resists rotation about the elongated direction, permitting fastener 101 and needle 109 to have a discernable mutual orientation. This embodiment is particularly useful for locating and placing fastener 101 in a preferred orientation, if so desired. For such uses, it may be advantageous to use a unitary flexible member 107 such as a strand of nitinol wire.

Tissue connector assembly 100 provides for the delivery of fastener 101 to a site in a tissue for fastening. Specifically, fastener 101 is releasably constrained or otherwise held in an open configuration as shown in FIG. 1 to deliver the fastener to a particular tissue site. Fastener 101 has a plurality of elements that, upon delivery, compress with a clipping action tissue through which it is placed. Prior to being placed in a tissue for fastening, fastener 101 is held in place by delivery device 110, or more specifically by holder 103. Holder 103 provides for retaining fastener 101 with arms or a stopper 102 that protrudes away from holder 103 and has a shape useful in positioning fastener 101 against a tissue that assembly 100 is threaded through (not shown). Thus stopper 102 is generally perpendicular or transverse to the elongated direction of assembly 100 and may have portions to facilitate placing fastener 101 by curving towards holder 103, for example. As described below, fastener 101 may be a self-closing fastener that is held for delivery by holder 103 to a tissue or to a layer of tissues (not shown in FIG. 1), and that upon removal from delivery device 110 is left attached to the tissue, while the delivery device is removed. Fastener 101 may thus include one or more self-closing, opposable elements that are held in a restrained configuration by delivery system 110, are positioned on opposite sides of a tissue, and are the released from delivery device upon the proper application of force, allowing the elements to relax towards an unrestrained configuration and to opposably approach other fastener elements to compress tissue placed or caught therebetween.

One important feature of assembly 100 is stopper 102 which provides for positive seating of fastener 101 against a tissue, while another important feature is the releasable holding of fastener 101 and the self-closing action that causes the fastener to assume a shape useful for compressing tissue. The fastener 101 is thus held in one configuration suitable for delivering the fastener to a tissue site through an opening such as a piercing and, upon release, transform towards a second configuration suitable for compressing the tissue. One embodiment of the inventive fastener uses material that can repeatably deform between the two configurations. The fastener can thus be fabricated or heat treated to assume the relaxed, closed configuration, and can be deformed into the open configuration, and upon delivery will conform to the closed configuration.

The tissue connector assembly 100 thus provides for placing a fastener 101 at the correct position within a tissue for fastening and the delivery of the fastener 101 at a tissue site, for joining tissue with opposable members, and removal of delivery device 110, specifically needle 109, flexible member 107, transition piece 105 and holder 103 from fastener 101.

An alternative tissue connector assembly 600 is shown in FIGS. 6A and 6B as a perspective view and a cross-sectional view, respectively. Assembly 600 has a fastener 601 coupled directly to a needle 609. Specifically needle 609 form a part of a delivery device 610, which further includes a fastener holding section 603 adapted to retain fastener 610. Fastener 601 is a fastener of the present invention, such as fastener 101 or other fasteners as described in detail subsequently. In general, the needle 609 has a sharp pointed tip 611 at its distal end for penetrating tissue. The needle 609 may be bent as shown in FIG. 6, for example. The distal end of the needle 609 is preferably rigid to facilitate penetration of tissue. The remaining length of the needle 609 may be rigid or flexible to facilitate movement of the needle through the tissue as further described below. The tip 611 of the needle 609 may be conical, tapered, or grounded to attain a three or four facet tip, for example. The needle 609 may be made from stainless steel or any other suitable material, such as a polymeric material. It is to be understood that the needle 609 may have a shape or radius of curvature other than the one shown, without departing from the scope of the invention. The needle 609 may be integrally formed with holder 603 or may be swaged, welded, threadably attached, or attached by any other suitable means to the holder.

Various fasteners, holders and delivery devices and methods will now be described in greater detail to illustrate, without limiting in the scope of the invention, devices and methods that achieve the aspects, objects and advantages of the present invention.

Clip and Holder Embodiment and Operation

There are many fasteners and fastener delivery systems that fall within the scope of the claimed invention. As an illustration of one fastener and delivery system, and in particular a fastener and fastener holder, is presented with reference to a fastener 101. Fastener 101 is can be delivered to a tissue site, for example, with the delivery system 100 of FIG. 1, and in particular is a self-closing fastener restrained by holder 103. One particular embodiment of assembly 100 is shown with reference and without limitation, to FIGS. 2, 3, and 5. In particular, a fastener is constructed as a fastener 200 shown as a particular embodiment of fastener 101 or 601, with a pair of stoppers or distal arms 210 serving the function of stopper 102 of FIG. 1. Fastener 200 is constructed of a flexible material that can assume a variety of configurations, enabling it to provide a compressive force on tissue by passing the fastener though the tissue and presenting opposable arms at locations near the location through which the fastener passes. Alternative fastener embodiments within the scope of the present invention are presented below and include, but are not limited to, a fasteners that include one or more opposable elements, fasteners having differing number of opposable elements on opposing sides, fasteners having elements that bend to compress tissue from one or both sides, fasteners that include multiple clipping elements of differing shape, clipping forces or symmetry, and fasteners of unitary or modular construction.

In addition, the various fastener elements or arms may be attached at any position that allows the transfer of force to opposable arms while positioning opposable elements on opposite sides of the tissue. Holder 240 is a holder 103 adapted to retain fastener 200 in an open configuration for delivery to a tissue site, and allows for release of the clip for removal of delivery device 110 to allow the fastener to revert towards a relaxed state that provides compressive forces to a tissue. Alternative holder embodiments within the scope of the present invention are presented below and include, but are not limited to tubular structures, wire clip structures, and suture.

Returning now to a specific embodiment of the present invention, FIG. 2A–C show a fastener 200 held by holder 240 (as in perspective view FIG. 2A and distal end view FIG. 5), being removed from the holder (FIG. 2B) and fully removed from the holder (FIG. 2C). FIG. 3 shows a cross-sectional view 3—3 of FIG. 2A, showing fastener 200 engaged within holder 240, and FIG. 5 is a distal end view 5—5, also of FIG. 2A. Fastener 200 comprises a pair of clips 231 and 233 each including one of the pair of stopper or distal arms 201, and one of the pair of terminator or proximal arms 203. Each of arms 201 and 203 has a free end, as in stopper or distal ends 206 and terminator or proximal ends 204, and is connected to other arms through a connecting stem 205. Terminator arms 203 are in general flexible while stopper arms 201 may be flexible and are adapted to transfer distally directed farces through fastener 101 to the terminator arms. The range of motion of terminator arms 203 are best considered in relation to FIG. 2 which shows the removal of fastener 200 from holder 240. Holder 240 includes a generally cylindrical tube 207 having an inner surface 301 forming a lumen 209 at distal end 211 for accepting fastener 101. Terminator arms 203 are bendable to allow a change in shape between open configuration 210 and closed configuration 220. Thus FIG. 2A shows the pair of terminator arms 203 in open configuration 210 placed within lumen 209. Terminator arms 203 lie within tube 207, while stopper arms 201 protrude radially away from holder 240.

Open configuration 210 is particularly useful for delivery of fastener 200 restrained within tissue connector apparatus 100, allowing two terminator arms 203 to be inserted through a tissue opening prior to closing the fastener, as described subsequently. FIG. 2B shows a step in the removal of fastener 200 from holder 240 as indicated by the opposing arrows during which fastener 200 generally maintains open configuration 210. FIG. 2C shows a relaxed configuration 220 has terminator ends 204 and stopper ends 206 opposably approaching to within a distance S about a line L, as shown in FIG. 2C. Terminator arms 203 can be straightened, forcing fastener 200 into an open configuration 210. The shape of fastener 200 promotes the bending of terminator arms 203 and allows stopper arms 201 to resist forces in the distal direction, and allows the formation of pair of opposable arms forming a pair of clips 231 and 233, as in FIG. 2C. As will be discussed subsequently, this clip embodiment is particularly useful for compressing tissue any material near line L of thickness greater than S. In addition, alternative clip embodiments will be presented subsequently that can be used to otherwise compress tissue between stopper arms and terminator arms over a larger or smaller area or with greater or smaller forces.

One particularly useful class of materials are nickel titanium (nitinol) based alloys. In addition to being biocompatible, nitinol under the right conditions is superelastic and can be repeatably deformed to a greater extent than most metals. The nitinol may include additional elements which affect the yield strength of the material or the temperature at which particular pseudoelastic or shape transformation characteristics occur. Nitinol exhibits a phase transition between two solid phases: martensite, which is generally stable at low temperatures, and austenite, which is generally stable at high temperatures The transformation exhibits hysteresis, and upon cooling to temperatures below the $M_f$ temperature the martensite phase is stable, while upon heating austenite is stable at temperatures above the $A_f$ temperature.

At temperatures slightly above the $A_f$ transformation temperature, the shape memory alloy exhibits pseudoelastic (superelastic) behavior when deformed. This is due to the particular mechanical properties of the various phases and the effect of phase transitions on the stress-strain curve of the alloy. In particular, martensite is more deformable and less strong than austenite. At temperature slightly above the $A_f$ transformation temperature, the application of stress can cause a phase change of austenite into martensite. As the stress is removed, the material undergoes a martensitic to austenitic conversion, and springs back to its original undeformed configuration. At temperature slightly above the $A_f$ transformation temperature Nitinol thus behaves "superelastically." In addition, the material exhibits a shape memory effect, in that a heat treated element having nitinol in the austenite phase can then be cooled to a temperature were at least a portion of the element includes martensite, the element can be reconfigured into a shape in which the martensite is plastically deformed, and then the element can be heated above the $A_f$ transformation temperature allowing the martensite to change phase back to austenite and causing the element to revert to the heat treated configuration.

Thus, one method of using a nitinol alloy as material for the inventive fasteners is to choose an alloy having a transformation temperature $A_f$ that is just below the temperature at which the fastener is to be used in a tissue, thus permitting, for example, from as a superelastic material, permitting elastic deformation over a very wide range of shape. A fastener 101 is heat treated, while maintained in what will become the "relaxed configuration" to produce a fastener that is predominantly austenite. Fastener 101 is then cooled to a temperature at which at least a portion of the fastener undergoes the phase change to martensite, is deformed and inserted into holder 103, and warmed to above the $A_f$ temperature. Upon warming, fastener 101 attempts to return to the relaxed configuration, and thus the transition arms are forced against the interior surface of holder 103. The fastener 101 will then stay coupled to holder 103 until pulled apart as described below. For normal surgical procedures, the fastener should have a transition temperature slightly below body temperature, while for procedures performed at lower temperatures, a lower transition temperature may be appropriate. For example, with a stopped heart condition where cold cardioplegia has been injected for temporary paralysis of the heart tissue, a transition temperature as low as 8–10 degrees Celsius may be useful.

Another important aspect of the present invention is the delivery of a "self-closing" fastener that if otherwise unconstrained will, upon release, assume an relaxed configuration. The discussion that follows illustrates the inventive fastener exhibiting some of the aspects of a self-closing fastener. Specifically with reference to the tissue connector assemblies 100 or 600 having a self-closing fastener such as fastener 200, consider the fastener formed of an elastic material in closed configuration 220 is shown in FIG. 3 in cross-section 3—3 of FIG. 2A. The removal of fastener 200 from the remaining assembly 110 results from the interaction of the fastener and holder 240 along with applied external forces to the fastener and holder. Terminator arms 203 can be manufactured from nitinol and operated slightly above the $A_f$ transition temperature, allowing use of the superelastic properties of that material and allowing for bending of fastener 200 between closed configuration 220 to open configuration 210. Alternatively, terminator arms 203 can be constructed of an elastic material.

One technique for manufacturing the inventive fastener from nitinol forms the fastener from nitinol wire or sheet. The fastener is preferably produced from a sheet of nitinol by flat-annealing the sheet, laser-cutting or photo-etching the shape from the sheet, de-burring or polishing the fastener, and heat treating the fastener to achieve desirable superelastic properties and surface conditions. The dimensions of the fastener are governed by the tissue thickness and elastic or superelastic properties of the fastener material that allow for predictable forces to be transferred to the tissue. Thus for example, sheet thickness t can range from 0.001 to 0.125 inches, with a thickness of 0.003 to 0.015 inches preferable. Alternatively, the fastener can be fashioned from wire by winding the wire on a fixture or mandrel, heat treating to set the desired shape, cutting the wire into individual components with burr-free ends, and connecting the components by welding or crimping to form a complete fastener. Useful wire sizes ranges are generally below 0.010" in diameter, with diameters of 0.002" to 0.008" being particularly useful for vascular attachments. Fastener 101, and fastener 200 in particular, can thus include, but are not limited to a unitary construction of a sheet of material of thickness t (as shown in FIG. 5) having arms 201 and 203 cut to form closed configuration 220 as shown, or can be formed of wires as pairs of proximal and distal arms and attached together, or from four separate arms attached near a central portion, forming a bridge as in connecting stem 205. When assembled and heat treated to assume closed configuration 220, stopper ends 206 and terminator ends 204 approach each other to within a spacing S that is preferably less than the total thickness of tissue to be connected, for example S may be a large as 0.250 inches so that two layers of tissues each 0.180 inches can be fastened. Ends 204 and 206 are spaced a distance less than 0.250 inches apart with connecting stem 205 centrally located. Terminator arms 204 can thus be straightened to fit within holder 103 having an inner diameter D of 0.005 to 0.250 inches, and preferably having a diameter of less than 0.025 inches, such as 0.007 inches. The arm thickness A of the more flexible components are sized to permit the clips to transfer a useful force while not overstressing the material on transitioning, from an open to a closed configuration. Values of A greater than 0.002" provide a thickness that is both flexible and provides a useful compressive force.

The open configuration 210 includes terminator arms 203 brought together by application of a pair of forces F on terminator ends 204 that pull the ends towards one another as shown in FIG. 3. Fastener 200 is thus under stress due to the deformation of terminator arms 203 from the closed configuration 220. Terminator ends 204 contact inner surface 208 at contact points 301, generating a force F at contact points 301 depending on the shape of inner surface 208 and the shape and state of fastener 200. The removal of fastener 200 from the remaining assembly 110 results from the interaction of fastener and holder 240 along with applied external forces to the fastener and holder. For a cylindrical inner surface 208 such as is shown in FIG. 3, the force required to extract fastener 200 from holder 240 is approximately constant. Upon pulling fastener 200 from holder 240, a frictional force will resist the release of the fastener due to the motion shown as the arrows in FIG. 2B. The amount of friction can be controlled by modifying the inner surface, for example by having rough or smooth portions, or by contouring the surface. Once terminator ends 204 no longer contact inner surface 208, the force on terminator arms 204 is removed and fastener 200 can deform towards closed configuration 220.

The presence a tissue or other members to be fastened (near line L) may restrain or otherwise force the fastener to assume other than the relaxed configuration. Preferably the fastener attempts to provide a force against the tissue that aids in sealing or healing of a tissue wound other tissue opening, or is otherwise useful for connecting attempts to assume or approaches a relaxed configuration.

Many of the previous features and methods of operation relate to the alternative tissue connector assembly 600 is shown in FIGS. 6A and 6B. Thus fastener 601 could be fastener 200 or other appropriately adapted fastener of the present invention, while fastener holding section 603 holder 240 or an equivalent. Fastener 600 is threaded through a tissue, as described previously, and when stopper 602 seat against a tissue, the fastener is released as previously described.

Methods of Using the Tissue Connector Assembly

The purpose of tissue connector assembly is, in part, to deliver fastener 101 through aligned tissue piercings such that the fastener passes through one tissue opening and applies compression to points distanced from the piercing. Referring to the use of a fastener 101 embodiment such as fastener 200, this entails placing the fastener such that closed configuration 220 is placed with connecting stem 205 through a piercing of one tissue or two or more stacked tissues, while compressing the tissue at points near one or more of the end of terminator ends 204 and stopper ends 206. Two particular methods for using tissue connector assembly 100 and similar assemblies to deliver fastener 101 will now be presented to illustrate providing fastener to a tissue site.

As a specific example of the use the inventive tissue connector assembly 100, consider the use of two specific tissue assemblies 800 and 900 as shown in FIGS. 8a and 9a for connecting two tissues in a surgical procedure. The general differences between assemblies 100, 800, and 900 involve the orientation of needle 109 to fastener 101. For the purposed of this example, the fastener 101 is fastener 200. In assembly 100 there is no specific orientation between the curvature of needle 109 and the orientation of stopper arms 201. In assemblies 800 and 900 flexible member 107 resists rotation about the elongated axis of the member to permit more precise positioning of the fastener with relation to the edges 705 and 707, and allowing specific types of attachments to be performed. In general, the use of the inventive fastener though assemblies 100, 800, or 900 as follows provides intima-to-intima contact with a self-closing fastener in one movement and without the need to tie suture.

More specifically, and for purposes of illustration not meant to limit the scope of the present invention, consider the use of assemblies 100, 800, or 900 to perform an anastomosis of a graft vessel 701 onto an artery 703 as shown prior to connecting tissue in FIG. 7A. In an end-to-side anastomosis procedure, the edge 707 of graft vessel 701 is attached to the wall artery 703 about a surgically provided arterial wall opening 705. The tissue connector assembly 101 may be used in open surgical procedures or in minimally invasive or endoscopic procedures for attaching tissue located in the chest, abdominal cavity, or retroperitoneal space. These examples, however, are provided for illustration and are not meant to be limiting to the type of tissues connected or to specific orientations of the fastener relative to the tissue.

The surgical technique of anastomosis includes cutting artery wall to produce an opening 705, and connecting edge 707 along or near the opening 705. The placement of tissue for attachment is illustrated in the sequence of FIGS. 7A–7B and 8A–8C, where the assembly 800 is used to place fasteners aligned perpendicular to the line of attachment and thus radial with respect to graft vessel 701, is shown in the attached vessels of FIG. 8C. FIG. 7A shows a tissue connector assembly such as assemblies 100, 800, or 900 threaded through graft 701 and artery 703, where needle 109 has been threaded through a first piercing 709 from the outside to the inside of graft 701, through opening 705, and through a second piercing 711 from the inside to the outside of artery 703. FIG. 7B shows the graft 701 placed onto artery 703. Alternatively, multiple tissue connector assemblies 101 can be placed about edge 707 and opening 705 in a procedure such as "parachuting" to provide more positive placement of the fasteners. In parachuting, the threading order is as in FIG. 7, with assembly 100, for example, threaded through graft 701 and seating fastener 101 against the graft, and then threaded through artery 703, permitting the graft and fastener to together approach the artery piercing 711. As an additional alternative, combinations of radially and circumferentially placed fasteners (as described below) may be used, or other types of fasteners or fasteners may be used or combined with sutures at different positions about the tissue attachment. For example, the tissue connectors described in the co-owned U.S. Patent Application for a BRIDGE FASTENER TISSUE CONNECTOR APPARATUS AND METHODS, filed Apr. 5, 2001 and assigned Ser. No. 09/828,322, included herein by reference, are particularly useful self-closing fasteners for securing the locally stressful attachment points at the heal or toe of the anastomosis.

Tissue connector assembly 800, or at least holder 240 portion of the assembly, is next pulled through piercings 709 and 711 to place the fastener radially as shown in FIG. 8A.

The two stopper arms 201 are differentiated as inner stopper arm 201A and outer stopper arm 201B. The orientation of curved needle 109 away from graft 701 radially aligns fastener 200. In the radial fastener placement, fastener 200 is positioned so that inner stopper arm 201A is radially aligned towards the center of graft 701, and the end of the outer stopper arm 201B is positioned radially away from graft 701, for example beyond the edge of opening 705 and edge 707. In bringing holder 240 through piercings 709 and 711, the vessels are each partially everted, bringing graft intima 801 in contact with artery intima 803, as shown in FIG. 8A. With fastener 200 so placed a longitudinal force is applied to separate the fastener from holder 240 as shown in FIG. 2B. One method for applying the required longitudinal force is to pull holder 240, flexible member 107 or needle 109 with fastener 200 seated against artery 703. This creates a countertension between fastener 200 and holder 240 that allows the fastener to slide out of the holder. An alternative method for affecting separation of fastener 200 and holder 240 is to provide an added force by placing the tips of a pair of pliers or other handy surgical implements on the opposite side of the tissue and against the fastener as illustrated in FIG. 10. With the holder 240 removed, fastener 200 tends towards closed configuration 220, or specifically towards fastened configuration 230 as shown in FIG. 8B. Inner stopper arm 201A approaches the corresponding one of terminator arms 203, compressing a tissue portion 805 therebetween with intima-to-intima contact. The resulting force from tissue contacts causes the fastened configuration to be slightly more open then closed configuration 220 may include the bending of stopper arms 201 from the closed configuration. The stopper pair of arms 201B may or may not compress tissue (they are shown in FIG. 8B as meeting past the tissue edges and thus not compressing tissue). The clip is additionally anchored by central portion 205 passing through piercings 709 and 711. Multiple clips 101 or dual clips 200 or other types of self closing clips can likewise be placed to form a series of intima-to-intima contacts about the periphery of the anastomosis.

An alternative method for attaching tissue is illustrated in the sequence of FIGS. 7A–7B and 9A–9C, where the clip are aligned parallel to the line of attachment and thus circumferentially about the anastomosis, as shown in the attached vessels of FIG. 9C. As in the radial placement of FIGS. 8A–8C, the circumferential placement of a clip begins as shown in FIG. 7A with tissue connector assembly 900 threaded through graft 701 and artery 703, with needle 109 threaded through a first piercing 709 from the outside to the inside of graft 701, through opening 705, and through a second piercing 711 from the inside to the outside of artery 703, and FIG. 7B shows the graft 701 placed onto artery 703.

Tissue connector assembly 900, or at least holder 240 portion of the assembly, is next pulled through piercings 709 and 711 to place the clip radially as shown in FIG. 9A. With needle 109 curved away from graft 701, fastener 200 is placed circumferentially on the anastomosis. Specifically, the two stopper arms 201 are circumferentially placed approximately the same distance from edge 707. In bringing holder 103 through piercings 709 and 711, the vessels are each partially everted until graft intima 801 contacts artery intima 803, as shown in FIG. 9A. With fastener 200 so placed, a longitudinal force is applied to separate the clip from holder 240, as shown in FIG. 2B. The force may either be applied by pulling on the holder 240 or attached components or by applying additional force, as through pliers, as described previously.

With the holder 240 removed, fastener 200 tends toward closed configuration 220 and assumes fastened configuration 232 as shown in FIG. 9B. As noted previously, the forces on the closed clip are not those of the relaxed or closed clip 220, and thus one or more arms may be deformed outwards from the relaxed configuration. Specifically, terminator arms 201 approach corresponding proximal arms 203, compressing tissue portions 807 and 809 therebetween with intima-to-intima contact. The clip is additionally anchored and located by connecting stem 205 passing through piercings 709 and 711. Multiple clips 101 or dual clips 200 can likewise be placed to form a series of intima-to-intima contacts about the periphery of the anastomosis as shown in FIG. 9C.

The circumferential placement, as shown in FIG. 9C, and the radial placement as shown in FIG. 8C both have advantages for attaching tissue. The circumferential placement, for example, provides two compression points with a single piercing of the two tissues, and thus minimizes the number of clips needed for an anastomosis. The radial placement minimizes the intraluminal exposure of the clip to the interior of the vessels and may have better intima-to-intima contact. The radial and circumferential placement may be combined on an anastomosis to take advantage of the various orientations. Thus for example radial placement could be used at the toe of the anastomotic attachment for added strength, while circumferential placement could be used on the sides to minimize the number of fasteners.

Alternative Clip Embodiments

Several alternative fastener embodiments of fastener 101 or 601 are presented in FIGS. 11–17. FIGS. 11A–11B are perspective views of a first alternative fastener embodiment a fastener 1100, where FIG. 11A is a view of the fastener in a closed configuration 1120, and FIG. 11B is a view of the fastener as it clips tissue in a fastened configuration 1130, which is the configuration assumed after insertion into a pair of tissues T1 and T2 As with the embodiment of FIG. 2, fastener 1110 includes a first clip 231 and a second clip 233. Each of clip 231 and 233 has a pair of stopper arms 1101 for seating against tissue and a pair of terminator arms 1103 for bending into holder 103. While the embodiment of FIG. 2 provides compression across opposing ends 204 and 206, many of the alternative embodiments provide compression between ends and opposing arms or between opposing arms. These variations in design allow for tailoring fasteners to produce different amounts of compression or to distribute the compression differently over the tissue.

The first alternative embodiment of a fastener 1100 is shown in FIGS. 11A–11B having stopper arms 1101 protruding radially outwards from connecting stem 1105 while terminator arms 1103 are similar to arms 203 and apply a terminator ends 1104. Dual clip 1101 thus presents surface 1102 to tissue T1 with connecting stem 1105 passing through tissues T1 and T2. Terminator arms 1103 present terminator ends 1104 against tissue T2. Tissues T1 and T2 are compressed between terminator ends 1104 and a compression portion 1107 of stopper arms 1101.

The second alternative embodiment of a fastener 1200 is shown in FIGS. 12A–12B, where FIG. 12A is a view of the fastener in a closed configuration 1220, and FIG. 12B is a view of the fastener as it clips tissue in a fastened configuration 1230. Dual fastener 1200 has stopper ends 1206 that more closely approach terminator edge 1211 than terminator ends 1204. This configuration provides a higher compressive force than does the fastener 200 by having a closed configuration 1220 that traps tissue T1 and T2 more tightly between the stopper arms 1201 and terminator arms 1203.

The third alternative embodiment of a fastener 1300 is shown in FIGS. 13A–13B, where FIG. 13A is a view of the fastener in a closed configuration 1320, and FIG. 13B is a view of the fastener as it clips tissue in a fastened configuration 1330. Dual fastener 1300 has a circular stopper 1306 and a circular shaped pair of terminator arms 1303. As shown in FIG. 13B, fastened configuration 1330 provides compression over a greater area than either of the previously described clips by compressing tissues T1 and T2 between nearly the entire presented arms of the terminator and stopper arms.

A fourth alternative embodiment of a fastener 1400 is shown in FIG. 14 in a closed configuration 1420. Fastener 1400 and the subsequent embodiments differ from the previous embodiments in that the clips 231 and 233 are attached by a cross member 1410, which bridges distal arms 1401, as opposed to the embodiment of FIG. 2, for example, in which clips 231 and 233 have a common connecting stem 205. Since connecting stem 205 structurally transfers the forces of both clips 231 and 233 in embodiments having a connecting stem, the stresses in stem 205 include the stress associated with each of the clips. The use of a cross member 1410 isolates the stress in each of clips 231 and 233, allowing for greater unyielding displacements of individual clips 231 and 233. In addition to the inclusion of cross member 1410, clips 231 and 233 apply forces asymmetrically. Specifically, proximal ends 1403' and 1403" differ in length, with distal end 1404' of clip 231 extending more distally than does proximal end 1404" of clip 233. Clip 231 of the fourth embodiment 1400 is thus configured to compress a greater surface area of tissue (not shown) or to provide a greater tissue compressive force.

A fifth alternative embodiment of a fastener 1500 is shown in FIG. 15 in closed configuration 1502. Fastener 1500 is similar to fastener 1300, with the substitution of a cross member 1510 for connecting stem 1305 and asymmetric proximal arms 1503' and 1503", allowing clip 231 of fastener 1500 to provide a greater compressive force than clip 233 of fastener 1500.

A sixth alternative embodiment of a fastener 1600 is shown in FIG. 16 in closed configuration 1620. Fastener 1600 has enlarged distal arms 1601 joined by cross member 1610 and having wrap-around proximal arms 1603, providing for greater tissue contact than is possible with many of the previous designs.

A seventh alternative embodiment of a fastener 1700 are shown in the several views of FIG. 17. Specifically, FIG. 17A is a view of the fastener in a closed configuration 1720, FIG. 17B is a view of the fastener in an open configuration 1710, FIG. 17C is a view of the fastener placed for fastening, and FIG. 17D is a view of the fastener in a fastened configuration 1730. FIG. 17A shows the distal arms 1701 and proximal arms 1703 attached with cross member 1710 and forming the two clips 231 and 233 of fastener 1700. Unlike the other fastener embodiments 200, and 1100–1600, fastener 1700 has both proximal arms 1703 and distal arms 1701 in closed configuration 1720 protruding proximally. As discussed subsequently, this configuration of arms allows both the proximal and distal arms to act as springs to provide greater compression to tissue T1 and T2. FIG. 17B shows fastener 1700 in open configuration 1710. As in the previous embodiments, proximal arms 1703 are straightened and held in place by a holder 1740. Distal arms 1701 curve back towards holder 1740, presenting most proximally surfaces 1750.

FIG. 17C shows fastener 1700 in open configuration 1710 as placed through piercing P in tissues T1 and T2. Proximal arms 1703 are led through piercing P by holder 1740, while surfaces 1750 contact tissue T2. As fastener 1700 is further pulled through piercing P, distal arms 1701 compress against tissue T2, and as proximal arms 1703 are released from holder 1740, the proximal arms spring back towards T1, assuming fastened configuration 1730 of FIG. 17D. In addition to providing compressive forces on both tissue surfaces, fastener 1700 can be configured to clip tissues of nearly any thickness, since the unrestrained arms attempt to assume closed configuration 1720. Since the fastened configuration 1730 and closed configuration 1720 have reversed longitudinal placement of the distal arms 1701 and proximal arms 1703, the arms can oppose one another and clip tissue of nearly any thickness, the inventive clip may have more than two pairs of stopper and terminator arms, for example three or more pairs of arms arranged about one or more centrally located connecting stems, or the stopper end could be a disc shape, radially protruding member that presents half of the opposable arm configuration to the tissue. Other embodiments within the scope of the present invention include fasteners that, when viewed from the proximal or distal ends, include clips that are not arranged symmetrically. Thus for example, a fastener when viewed from the end, as in FIG. 5 could have a 90 degree angle between the planes formed by arms of clips 231 and 233.

Alternative Holder Embodiments

Three alternative holders 103 are shown in FIGS. 4A–4C where the force F, and thus the frictional force for removal, are altered by changing the inner surface 208. For reference in the following discussion, the embodiment of FIG. 3 has a constant diameter inner cylindrical surface 208, resulting in a constant force for extracting fastener 101 after the initial static frictional force is overcome. The alternative embodiments of FIG. 4 have the inner surface 208 modified to change the force required to extract fastener 101. The change in force with extraction has implications on how easy it is to seat the fastener without it being accidentally actuated and on the "feel" of the use of the fastener.

The first alternative holder embodiment of FIG. 4A has an inner surface 208A with a protrusion 401 at the distal end of holder 103A. Protrusion 401 provides an added barrier to the removal of fastener 101. If the friction coefficient of surface 208A were constant, for example, then a constant force would be required to axially slide fastener 101 to the distal holder end 211. Pulling fastener 101 over protrusion 401 requires further bending of proximal arm 203, resulting in a higher normal force. An increased normal force results in a higher frictional force, and thus the extraction of fastener 101 from the end of holder 103B requires a slightly higher force.

The second alternative holder embodiment of FIG. 4B has an generally cylindrical inner surface 208B with a inner protrusion 402 positioned to positively seat the fastener in the fully retained position of FIG. 2A. In this embodiment a higher force is required to initiate the ejection of fastener 101 from holder 103, followed by a constant force. The third alternative holder embodiment of FIG. 4C has a force requirement similar to the second alternative embodiment. As shown in FIG. 4C, inner surface 208C has recess 403 for retaining terminator ends 204. Upon initiating extracting fastener 101, terminator ends 204 first move inwards and are then held at a constant diameter. The modification of the inner surface 208 by changes in contour or friction coefficient by a variety of means would be obvious to those in the art, and could include bumps, ridges, changes in surface finish, and could include multiple devices to modify the friction of fastener 101 as it is pulled from holder 103. Thus for example there could be a required high starting force and ending force to permit a user of the fastener to feel when the fastener is being released and when the release is complete.

While the previous discussion was directed to modifications of holder 103 that describe circumferentially uniform changes to inner surface 208 that affect the longitudinal friction force restraining fastener 101, the same devices could be placed with circumferential orientations to allow the fastener to be positively located within the holder. Thus for example, the holders in FIGS. 8a and 9a could provide for positively fixing the rotational orientation of the held fastener within the holder.

In addition to generally cylindrical holders such as holders 103, 240, 1740, fastener can be configured for holding using other techniques. Thus for example, FIG. 18A shows a fastener 1700' in closed configuration 1720', which is fastener 1700 modified with the addition of notches 1801 near the ends proximal arms 1703". FIG. 18B shows fastener 1700' with a length of suture 1840A wrapped about proximal arms 1703' and through notches 1801 to restrain the fastener. Holder 1840A can be released by cutting the suture, for example. FIG. 18C shows fastener 1700' restrained by a holder clip 1840B which fits into notches 1801 and has a hole or ring 1841 through which suture 107 can be attached to form a tissue connector apparatus 100.

Additional alternative holder embodiments include, but are not limited to a holder that is radially flexible, where the flexing of the holder causes a change in inner surface shape the ejects the clip from the holder and a holder in the form of an open structure that retains the terminator ends in a detent structure, a holder that is in the shape of a clip that retains the proximal arms, and a holder formed of suture by wrapping the suture about the proximal arms and is released upon cutting the suture. Alternatively, other release mechanisms could be incorporated into holder 103 for holding and releasing fastener 101, and the clip geometry and/or surface condition may interact with the holder to either restrain the clip or provide a "feel" back to the user of the state of the fastener with respect to the holder.

The invention has now been explained with regard to specific embodiments. Variations on these embodiments and other embodiments may be apparent to those of skill in the art. It is therefore intended that the invention not be limited by the discussion of specific embodiments. It is understood that the examples and embodiments described herein are for illustrative purposes only and that various modifications or changes in light thereof will be suggested to persons skilled in the art and are to be included within the spirit and purview of this application and scope of the appended claims.

We claim:

1. Apparatus for fastening tissue comprising a fastener having a stopper, where said stopper includes one or more distal members, and a plurality of proximal members flexibly attached to said stopper, where said fastener has a fastened configuration in which said plurality of proximal members oppose at least a portion of said stopper, and an open configuration where said fastener is openly restrained from said fastened configuration to accept tissue, such that tissue positioned within said open configuration is compressed when said fastener is unrestrained, wherein at least one of said plurality of proximal members of said fastened configuration has a distally oriented end, and wherein said distally oriented end of said fastened configuration opposes at least a portion of said stopper, further including a piercing member having a tip and a hollow end for accepting at least a portion of said plurality of proximal members.

2. The apparatus of claim 1, wherein said fastener is nitinol.

3. Apparatus for fastening tissue comprising:
a fastener having a stopper, where said stopper includes one or more distal members, and a plurality of proximal members flexibly attached to said stopper, said fastener having a fastened configuration where at least one of said plurality of proximal members opposes at least a portion of said stopper; and
a restraint mechanism to releasably restrain said plurality of proximal members of said fastener in an open configuration away from said fastened configuration without restraining said one or more distal members, such that tissue is placeable within said releasably restrained fastener, and where that upon releasing said fastener from said restraint mechanism, said plurality of proximal members return toward said fastened configuration to compress said tissue, further including a piercing member having a tip and a hollow end for accepting at least a portion of said plurality of proximal members.

4. The apparatus of claim 3, wherein said fastener is nitinol.

5. A tissue connector assembly for fastening tissue or layers of tissues having an external distal surface and an external proximal surface, comprising:
a fastener having, where said stopper includes one or more distal members, and a plurality of proximal members flexibly attached to said stopper, where at least one of said plurality of proximal members has a fastened configuration opposing at least a portion of said stopper; and
a piercing member for piercing tissue and having an elongated member and a holder mechanism that is releasably holding said plurality of proximal members in an open configuration, and where said stopper extends transversely away from said elongated member.

6. The assembly of claim 5, wherein said fastener includes two proximal members.

7. The assembly of claim 5, wherein said fastener comprises nitinol.

8. The assembly of claim 5, wherein said fastener is of unitary construction.

9. The assembly of claim 5, wherein said plurality of proximal members are elongated members.

10. The assembly of claim 5, wherein said one or more distal members each comprise a disk-shaped member.

11. The assembly of claim 5, wherein the number of proximal members is equal to the number of distal members.

12. The assembly of claim 11, wherein said fastener has a longitudinal orientation having a centerline, and wherein said proximal members and said distal members are approximately symmetric about said centerline.

13. The assembly of claim 5, wherein a portion of said stopper has a proximally oriented surface, wherein said stopper is a spring, and wherein said stopper is distally deformable for application of force to said tissue.

14. The assembly of claim 5, wherein at least one of said plurality of proximal members of said fastened configuration has a distally oriented end, and wherein said distally oriented end of said fastened configuration opposes at least a portion of said stopper.

15. The assembly of claim 5, wherein at least a portion of said stopper has proximally oriented ends and wherein at least a portion of said plurality of proximal members of said fastened configuration oppose at least one of said proximally oriented ends.

16. The assembly of claim 5, wherein at least one of said plurality of proximal members of said fastened configuration has a distally facing surface, wherein at least a portion of said stopper has a proximally facing surface, and wherein at least a portion of said distally facing surface of said fastened configuration opposes said proximally facing surface.

17. The assembly of claim 5, wherein said piercing member has a tubular portion that forms said mechanism.

18. The assembly of claim 17, wherein said mechanism has an inner surface for restraining said plurality of proximal members.

19. The assembly of claim 18, wherein said mechanism releases said fastener when said fastener is pulled from said mechanism.

20. The assembly of claim 18, wherein said mechanism releases said fastener when said mechanism is squeezed.

21. The assembly of claim 5, wherein said piercing member is flexible.

22. The assembly of claim 5, wherein said piercing member is nitinol.

23. A tissue connector assembly for fastening a tissue or layer of tissues having an external distal surface and an external proximal surface, comprising:
   a piercing member;
   a flexible member having a first end attached to said piercing member, and a second end; and
   a fastener releasably attached to said second end, said fastener having a stopper including one or more distal members, and a plurality of proximal members flexibly attached to said stopper, where at least one of said plurality of proximal members has a fastened configuration opposing at least a portion of said stopper, where said fastener is releasably attached to said flexible member with said plurality of proximal members in an open configuration having said stopper extending transversely away from said piercing member.

24. The assembly of claim 23, wherein fastener includes two proximal members.

25. The assembly of claim 23, wherein said piercing member is flexible.

26. The assembly of claim 23, wherein said piercing member is nitinol.

27. The assembly of claim 23, wherein said flexible member is a suture.

28. The assembly of claim 23, wherein said flexible member is nitinol.

29. The assembly of claim 23, wherein said open configuration includes openly restraining said plurality of proximal members.

30. The assembly of claim 23, wherein said fastener is nitinol.

31. The assembly of claim 23, wherein said fastener is of unitary construction.

32. The assembly of claim 23, wherein said plurality of proximal members are elongated members.

33. The assembly of claim 23, wherein said one or more distal members each comprise a disk-shaped member.

34. The assembly of claim 23, wherein the number of proximal members is equal to the number of distal members.

35. The assembly of claim 34, wherein said fastener has a longitudinal orientation having a centerline, and wherein said proximal members and said distal members are approximately symmetric about said centerline.

36. The assembly of claim 23, wherein a portion of said stopper has a proximally oriented surface, wherein said stopper is a spring, and wherein said stopper is distally deformable for application of force to said tissue.

37. The assembly of claim 23, wherein at least one of said plurality of proximal members of said fastened configuration has a distally oriented end, and wherein said distally oriented end of said fastened configuration opposes at least a portion of said stopper.

38. The assembly of claim 23, wherein at least a portion of said stopper has proximally oriented ends and wherein at least a portion of said plurality of proximal members of said fastened configuration oppose at least one of said proximally oriented ends.

39. The assembly of claim 23, wherein at least one of said plurality of proximal members of said fastened configuration has a distally facing surface, wherein at least a portion of said stopper has a proximally facing surface, and wherein at least a portion of said distally facing surface of said fastened configuration opposes said proximally facing surface.

40. The assembly of claim 23, further including a holder that is attached to said flexible member second end and that is releasably holding said fastener.

41. The assembly of claim 40, wherein said holder is a suture.

42. The assembly of claim 40, wherein said holder is a restraint clip.

43. The assembly of claim 40, wherein said holder is a generally cylindrical tube having an opening for accepting at least a portion of said plurality of proximal members.

44. The assembly of claim 43, wherein said holder has an inner surface for restraining said plurality of proximal members.

45. The assembly of claim 40, wherein said holder releases said fastener when said fastener is pulled from said holder.

46. The assembly of claim 40, wherein said holder releases said fastener when said holder is squeezed.

47. A tissue connector assembly for fastening a tissue or layer of tissues having an external distal surface and an external proximal surface, comprising:
   a piercing member;
   a flexible member having a first end attached to said piercing member, and a second end;
   a restraint mechanism attached to said second end; and
   a fastener releasably attached to said restraint mechanism, said fastener having a stopper including one or more distal members, and a plurality of proximal members flexibly attached to said stopper, where at least one of said plurality of proximal members has a fastened configuration opposing at least a portion of said stopper, where said restraint mechanism releasably holds said plurality of proximal members of said fastener in an open configuration with said stopper extending transversely away from said piercing member.

48. The assembly of claim 47, wherein said fastener includes two proximal members.

49. The assembly of claim 47, wherein said piercing member is flexible.

50. The assembly of claim 47, wherein said piercing member is nitinol.

51. The assembly of claim 47, wherein said flexible member is a suture.

52. The assembly of claim 47, wherein said flexible member is nitinol.

53. The assembly of claim 47, wherein said fastener is nitinol.

54. The assembly of claim 47, wherein said fastener is of unitary construction.

55. The assembly of claim 47, wherein said plurality of proximal members are elongated members.

56. The assembly of claim 47, wherein said one or more distal members each comprise a disk-shaped member.

57. The assembly of claim 47, wherein the number of proximal members is equal to the number of distal members.

58. The assembly of claim 47, wherein said fastener has a longitudinal orientation having a centerline, and wherein said proximal members and said distal members are approximately symmetric about said centerline.

59. The assembly of claim 47, wherein a portion of said stopper has a proximally oriented surface, wherein said stopper is a spring, and wherein said stopper is distally deformable for application of force to said tissue.

60. The assembly of claim 47, wherein at least one of said plurality of proximal members of said fastened configuration has a distally oriented end, and wherein said distally oriented end of said fastened configuration opposes at least a portion of said stopper.

61. The assembly of claim 47, wherein at least a portion of said stopper has proximally oriented ends and wherein at least a portion of said plurality of proximal members of said fastened configuration oppose at least one of said proximally oriented ends.

62. The assembly of claim 47, wherein at least one of said plurality of proximal members of said fastened configuration has a distally facing surface, wherein at least a portion of said stopper has a proximally facing surface, and wherein at least a portion of said distally facing surface of said fastened configuration opposes said proximally facing surface.

63. The assembly of claim 47, wherein said restraint mechanism is a suture.

64. The assembly of claim 47, wherein said restraint mechanism is a restraint clip.

65. The assembly of claim 47, wherein said restraint mechanism is a generally cylindrical tube having an opening for accepting at least a portion of said plurality of proximal members.

66. The assembly of claim 65, wherein said restraint mechanism has an inner surface for restraining said plurality of proximal members.

67. The assembly of claim 47, wherein said restraint mechanism releases said fastener when said fastener is pulled from said restraint mechanism.

68. The assembly of claim 47, wherein said restraint mechanism releases said fastener when said restraint mechanism is squeezed.

69. A method for fastening a first tissue and a second tissue with a fastener delivered to said first and second tissues in a holder, said method comprising:

piercing the first tissue;

piercing the second tissue;

passing said holder through said piercings of said first and second tissues, where said fastener is releasably coupled to said holder, where said fastener has a stopper and a plurality of terminator arms, where said fastener has a coupled configuration releasably restraining said at least two terminator arms in said holder with said stopper extending approximately perpendicular from said holder, and where said fastener has a decoupled configuration where said plurality of terminator arms and said stopper are opposable across said first and second tissues;

seating said stopper of said coupled fastener against said first tissue; and decoupling said fastener, such that at least one of said terminator arms return towards said decoupled configuration and opposes said stopper across said first and second tissues.

70. A method for creating an intima-to-intima tissue contact between a first tissue and a second tissue each having an adventitia and an intima with a fastener delivered to said first and second tissues in a holder, said method comprising:

piercing the adventitia of a first tissue;

piercing the intima of a second tissue passing said holder through said piercings of the first and second tissues, where said fastener is releasably coupled to said holder, where said fastener has a stopper and at least two terminator arms, where said fastener has a coupled configuration releasably restraining said at least two terminator arms in said holder with said stopper extending approximately perpendicular from said holder, and where said fastener has a decoupled configuration where said at least two terminator arms and said stopper are opposable across said tissue at more than one location;

seating said stopper of said coupled fastener against said adventitia of the first tissue; and decoupling said fastener, such that at least one of said terminator arms returns toward said decoupled configuration and opposes said stopper across said first and second tissues, and such that the intima of the first tissue is in contact with the intima of the second tissue.

* * * * *